US010302972B2

United States Patent
McDonald et al.

(10) Patent No.: US 10,302,972 B2
(45) Date of Patent: May 28, 2019

(54) WAVEGUIDE TRANSMISSION

(71) Applicant: Pacific Biosciences of California, Inc., Menlo Park, CA (US)

(72) Inventors: Mark McDonald, Milpitas, CA (US); Aaron Rulison, Los Altos, CA (US); Paul Lundquist, San Francisco, CA (US); Tsuei-Lian Wang, Campbell, CA (US); Deborah Pao-Tung Kwo, Sunnyvale, CA (US); Shang Wang, San Carlos, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 15/003,589

(22) Filed: Jan. 21, 2016

(65) Prior Publication Data
US 2016/0216538 A1 Jul. 28, 2016

Related U.S. Application Data

(60) Provisional application No. 62/107,310, filed on Jan. 23, 2015.

(51) Int. Cl.
*G02F 1/01* (2006.01)
*G02B 6/00* (2006.01)
(Continued)

(52) U.S. Cl.
CPC ............ *G02F 1/011* (2013.01); *G02F 1/0126* (2013.01); *G02F 1/0147* (2013.01); *G01N 21/648* (2013.01)

(58) Field of Classification Search
CPC ............ G02B 6/34; G02B 2006/12147; G02B 2006/12121; G02B 2006/12142;
(Continued)

(56) References Cited

U.S. PATENT DOCUMENTS 4,711,955 A  12/1987 Ward et al.
4,933,206 A  6/1990 Cox
(Continued)

FOREIGN PATENT DOCUMENTS

EP  1871902 B1  10/2010
EP  1963530 B1  7/2011
(Continued)

OTHER PUBLICATIONS

Eid et al., "Real-Time DNA Sequencing From Single Polymerase Molecules," Science (2009) 323:133-138.
(Continued)

*Primary Examiner* — Kaveh C Kianni
*Assistant Examiner* — Hung Q Lam
(74) *Attorney, Agent, or Firm* — Robert H. Reamey

(57) ABSTRACT

We have seen that some waveguides exhibit variable and increasing back reflection of single wavelength illumination over time, limiting their effectiveness and reliability. We have developed approaches to improve the transmission of these waveguides. We have found that by modulating the illumination wavelength over a small wavelength range we can reduce or eliminate this back reflection from the waveguide. In addition, we describe the writing and erasing of gratings within SiON waveguides by forming standing waves. Methods, systems, instruments, and devices are described that provide improved transmission of light through such waveguides.

18 Claims, 13 Drawing Sheets

(51) Int. Cl.
  *G02B 6/12*  (2006.01)
  *G02B 6/10*  (2006.01)
  *G01N 21/64* (2006.01)

(58) Field of Classification Search
  CPC ........... G02B 2006/12138; G02B 2006/12107;
    G02B 5/1842; G02F 1/025; G02F 1/026;
    G02F 1/0147; G02F 1/011; G02F
    2203/055
  USPC .............. 385/1, 11, 12, 14, 15, 37, 129–132
  See application file for complete search history.

(56) References Cited

U.S. PATENT DOCUMENTS

| | | | |
|---|---|---|---|
| 5,001,050 A | 3/1991 | Blanco et al. | |
| 5,135,876 A | 8/1992 | Andrade et al. | |
| 5,143,854 A | 9/1992 | Pirrung et al. | |
| 5,198,543 A | 3/1993 | Blanco et al. | |
| 5,424,186 A | 6/1995 | Fodor et al. | |
| 5,439,647 A | 8/1995 | Saini | |
| 5,547,839 A | 8/1996 | Dower et al. | |
| 5,576,204 A | 11/1996 | Blanco et al. | |
| 5,623,338 A * | 4/1997 | Wickramasinghe ... | G01Q 60/22 250/310 |
| 5,624,711 A | 4/1997 | Sundberg et al. | |
| 5,648,245 A | 7/1997 | Fire et al. | |
| 5,674,716 A | 10/1997 | Tabor et al. | |
| 5,688,648 A | 11/1997 | Mathies et al. | |
| 5,714,320 A | 2/1998 | Kool | |
| 5,723,584 A | 3/1998 | Schatz | |
| 5,874,239 A | 2/1999 | Schatz | |
| 5,919,523 A | 7/1999 | Sundberg et al. | |
| 5,932,433 A | 8/1999 | Schatz | |
| 6,192,168 B1 | 2/2001 | Feldstein et al. | |
| 6,210,891 B1 | 4/2001 | Gupte et al. | |
| 6,210,896 B1 | 4/2001 | Chan | |
| 6,255,083 B1 | 7/2001 | Williams | |
| 6,258,568 B1 | 7/2001 | Nyren | |
| 6,261,808 B1 | 7/2001 | Auerbach | |
| 6,265,552 B1 | 7/2001 | Schatz | |
| 6,350,413 B1 * | 2/2002 | Reichert .......... | G01N 33/54373 385/12 |
| 6,399,335 B1 | 6/2002 | Kao et al. | |
| 6,437,345 B1 | 8/2002 | Bruno-Raimondi et al. | |
| 6,787,308 B2 | 9/2004 | Balasubramanian et al. | |
| 6,917,726 B2 | 7/2005 | Levene et al. | |
| 7,013,054 B2 | 3/2006 | Levene et al. | |
| 7,022,515 B2 | 4/2006 | Herron et al. | |
| 7,041,812 B2 | 5/2006 | Kumar et al. | |
| 7,056,661 B2 | 6/2006 | Korlach et al. | |
| 7,170,050 B2 | 1/2007 | Turner et al. | |
| 7,175,811 B2 | 2/2007 | Bach et al. | |
| RE39,772 E | 8/2007 | Herron et al. | |
| 7,315,019 B2 | 1/2008 | Turner et al. | |
| 7,405,281 B2 | 7/2008 | Xu et al. | |
| 7,476,503 B2 | 1/2009 | Turner et al. | |
| 7,486,865 B2 | 2/2009 | Foquet et al. | |
| 7,537,734 B2 | 5/2009 | Reichert et al. | |
| 7,626,704 B2 | 12/2009 | Lundquist et al. | |
| 7,630,073 B2 | 12/2009 | Lundquist et al. | |
| 7,692,783 B2 | 4/2010 | Lundquist et al. | |
| 7,714,303 B2 | 5/2010 | Lundquist et al. | |
| 7,715,001 B2 | 5/2010 | Lundquist et al. | |
| 7,763,423 B2 | 7/2010 | Roitman et al. | |
| 7,767,394 B2 | 8/2010 | Turner et al. | |
| 7,767,805 B2 | 8/2010 | Buzby | |
| 7,777,013 B2 | 8/2010 | Xu et al. | |
| 7,805,081 B2 | 9/2010 | Lundquist et al. | |
| 7,820,983 B2 | 10/2010 | Lundquist et al. | |
| 7,834,329 B2 | 11/2010 | Lundquist et al. | |
| 7,838,847 B2 | 11/2010 | Lundquist et al. | |
| 7,901,889 B2 | 3/2011 | Christians et al. | |
| 7,906,284 B2 | 3/2011 | Turner et al. | |
| 7,907,800 B2 | 3/2011 | Foquet et al. | |
| 7,931,867 B2 | 4/2011 | Korlach | |
| 7,932,035 B2 | 4/2011 | Korlach | |
| 7,935,310 B2 | 5/2011 | Korlach | |
| 7,961,314 B2 | 6/2011 | Lundquist et al. | |
| 7,968,702 B2 | 6/2011 | Wegener et al. | |
| 7,973,146 B2 | 7/2011 | Shen et al. | |
| 7,993,891 B2 | 8/2011 | Roitman et al. | |
| 7,993,895 B2 | 8/2011 | Eid | |
| 7,995,202 B2 | 8/2011 | Lundquist et al. | |
| 7,998,717 B2 | 8/2011 | Eid et al. | |
| 8,003,330 B2 | 8/2011 | Heiner et al. | |
| 8,053,742 B2 | 11/2011 | Lundquist et al. | |
| 8,058,031 B2 | 11/2011 | Xu et al. | |
| 8,071,346 B2 | 12/2011 | Eid et al. | |
| 8,133,672 B2 | 3/2012 | Bjornson et al. | |
| 8,133,702 B2 | 3/2012 | Shen et al. | |
| 8,137,942 B2 | 3/2012 | Roitman et al. | |
| 8,143,030 B2 | 3/2012 | Maxham et al. | |
| 8,149,399 B2 | 4/2012 | Lundquist et al. | |
| 8,153,375 B2 | 4/2012 | Travers et al. | |
| 8,182,993 B2 | 5/2012 | Tomaney et al. | |
| 8,193,123 B2 | 6/2012 | Rank et al. | |
| 8,198,023 B2 | 6/2012 | Ma et al. | |
| 8,207,509 B2 | 6/2012 | Lundquist et al. | |
| 8,247,216 B2 | 8/2012 | Zaccarin et al. | |
| 8,252,910 B2 | 8/2012 | Korlach et al. | |
| 8,252,911 B2 | 8/2012 | Bjornson et al. | |
| 8,257,954 B2 | 9/2012 | Clark et al. | |
| 8,274,040 B2 | 9/2012 | Zhong et al. | |
| 8,304,191 B2 | 11/2012 | Eid et al. | |
| 8,318,094 B1 | 11/2012 | Bayandorian et al. | |
| 8,335,029 B2 | 12/2012 | Monadgemi | |
| 8,343,746 B2 | 1/2013 | Rank et al. | |
| 8,370,079 B2 | 2/2013 | Sorenson et al. | |
| 8,388,982 B2 | 3/2013 | Kong et al. | |
| 8,420,366 B2 | 4/2013 | Clark et al. | |
| 8,465,699 B2 | 6/2013 | Fehr et al. | |
| 8,465,922 B2 | 6/2013 | Eid et al. | |
| 8,467,061 B2 | 6/2013 | McCaffrey et al. | |
| 8,501,922 B2 | 8/2013 | Otto et al. | |
| 8,906,660 B2 | 12/2014 | Kamtekar et al. | |
| 8,989,538 B2 | 3/2015 | Wolfgang et al. | |
| 9,062,091 B2 | 6/2015 | Bjornson et al. | |
| 9,116,118 B2 | 8/2015 | Turner et al. | |
| 9,238,836 B2 | 1/2016 | Korlach et al. | |
| 2003/0077610 A1 | 4/2003 | Nelson et al. | |
| 2003/0096253 A1 | 5/2003 | Nelson | |
| 2003/0162213 A1 | 8/2003 | Fuller et al. | |
| 2003/0190647 A1 | 10/2003 | Odera | |
| 2003/0215862 A1 | 11/2003 | Parce et al. | |
| 2004/0048300 A1 | 3/2004 | Sood et al. | |
| 2004/0152119 A1 | 8/2004 | Sood et al. | |
| 2004/0224319 A1 | 11/2004 | Sood et al. | |
| 2004/0241716 A1 | 12/2004 | Kumar et al. | |
| 2004/0259082 A1 | 12/2004 | Williams | |
| 2006/0088068 A1 | 4/2006 | Farrell et al. | |
| 2008/0080059 A1 | 4/2008 | Dixon et al. | |
| 2008/0241892 A1 | 10/2008 | Roitman et al. | |
| 2009/0118129 A1 | 5/2009 | Turner | |
| 2009/0208957 A1 | 8/2009 | Korlach et al. | |
| 2010/0003765 A1 | 1/2010 | Dixon et al. | |
| 2010/0047802 A1 | 2/2010 | Bjornson et al. | |
| 2010/0057185 A1 | 3/2010 | Melsheimer et al. | |
| 2010/0093555 A1 | 4/2010 | Bjornson et al. | |
| 2010/0221716 A1 | 9/2010 | Flusberg et al. | |
| 2010/0255488 A1 | 10/2010 | Kong et al. | |
| 2011/0059505 A1 | 3/2011 | Hanzel et al. | |
| 2011/0117637 A1 | 5/2011 | Gray et al. | |
| 2011/0183320 A1 | 7/2011 | Flusberg et al. | |
| 2011/0183409 A1 | 7/2011 | Newby et al. | |
| 2011/0244447 A1 | 10/2011 | Korlach | |
| 2011/0257040 A1 | 10/2011 | Turner et al. | |
| 2011/0257889 A1 | 10/2011 | Klammer et al. | |
| 2011/0278475 A1 | 11/2011 | Lundquist et al. | |
| 2012/0009567 A1 | 1/2012 | Fedorov et al. | |
| 2012/0015825 A1 | 1/2012 | Zhong et al. | |
| 2012/0021525 A1 | 1/2012 | Fehr et al. | |
| 2012/0034602 A1 | 2/2012 | Emig et al. | |
| 2012/0052488 A1 | 3/2012 | Yue et al. | |

(56) References Cited

U.S. PATENT DOCUMENTS

| | | | |
|---|---|---|---|
| 2012/0052506 | A1 | 3/2012 | Yue et al. |
| 2012/0052507 | A1 | 3/2012 | Shen |
| 2012/0058469 | A1 | 3/2012 | Shen |
| 2012/0058473 | A1 | 3/2012 | Yue et al. |
| 2012/0058482 | A1 | 3/2012 | Shen et al. |
| 2012/0071359 | A1 | 3/2012 | Sun et al. |
| 2012/0077189 | A1 | 3/2012 | Shen et al. |
| 2012/0085894 | A1* | 4/2012 | Zhong ............... G01N 21/648 250/227.11 |
| 2012/0115736 | A1 | 5/2012 | Bjornson et al. |
| 2012/0196279 | A1 | 8/2012 | Underwood et al. |
| 2012/0322666 | A1 | 12/2012 | Pham et al. |
| 2012/0322692 | A1 | 12/2012 | Pham et al. |
| 2013/0138358 | A1 | 5/2013 | Tang et al. |
| 2013/0309661 | A1 | 11/2013 | Bornhop |
| 2014/0005404 | A1 | 1/2014 | Yue et al. |
| 2014/0134610 | A1 | 5/2014 | Pham et al. |
| 2014/0179564 | A1 | 6/2014 | Korlach et al. |
| 2014/0199016 | A1* | 7/2014 | Grot .................... G02B 6/10 385/11 |
| 2014/0211202 | A1 | 7/2014 | Niewczas et al. |

FOREIGN PATENT DOCUMENTS

| | | |
|---|---|---|
| WO | 9106678 A1 | 5/1991 |
| WO | 9627025 A1 | 9/1996 |
| WO | 9905315 A2 | 2/1999 |
| WO | 2013055466 A1 | 4/2013 |
| WO | 2013121224 A1 | 8/2013 |

OTHER PUBLICATIONS

Herve et al. "Optical Technologies for Enterprise Networks," Intel Technology Journal (2004) 8(2):73-171.

Hill and Meltz, "Fiber Bragg Grating Technology Fundamentals and Overview," Journal of Lightwave Technology vol. 15, No. 8, Aug. 1997, pp. 1263-1276.

Hill et al., "Photosensitivity in Optical Fiber Waveguides: Application to Reflection Filter Fabrication," Appl. Phys. Lett. (1978) 32(10):647-649.

Hong et al., "Self-Assembly of a Dendron Through Multiple Ionic Interaction to Give Mesospacing Between Reactive Amine Groupe on the Surfact," Langmuir (2003) 19:2357-2365.

Khanna, et al., "Impact of ALD Grown Passivation Layers on Silicon Nitride Based Integrated Optic Devices for Very-Near-Infrareg Wavelengths" Optics Express 5684 (2014) 22(5), DOI: 10.1364/OE.22.005684.

Kokubun, "Wavelength Selective Integrated Device by Vertically Coupled Microring Resonator Filter," Photonics Based on Wavelength Integration and Manipulation, IPAP Books 2 (2005) pp. 303-316.

Kratzig et al., "Holographic Storage Properties of Electrooptic Crystals," SPIE International Conference on Holography Aplications (1986) vol. 673 pp. 483-488.

Levene et al., "Zero-mode Waveguides for Single-molecule Analysis at High Concentration" Science (2003) 299:682-686.

Lopez-Yglesias et al., "The Physics of Extreme Sensitivity in Whispering Gallery Mode Optical Biosensors," J Applied Physics (2012) 111, 084701; doi: 10.1063/1.3698319.

Mok et al., "Storage of 500 High-Resolution Holograms in a LiNbO3 Crystal," Optics Letters (1991) 16(8):605-607.

Mok et al., "System Metric for Holographic Memory Systems," Optics Letters (1996) vol. 21, No. 12, pp. 896-898.

Morchetti, "Roughness Induced Backscattering in Optical Silicon Waveguides," Physical Review Letters (2010) 104, 033902.

Ruffin, "Stimulated Brillouin Scattering: An Overview of Measurements, System Impairments, and Applications," NIST-SOFM (2004), p. 1-6.

Ueno et al., "High UV Sensitivity of SiON Film and Its Application to Center Wavelength Trimming of Microring Resonator Filter," IEICE Trans Electron (2005) vol. E88, No. 5, pp. 998-1004.

Warren et al. "Ultraviolet Light Induced Annihilation of Silicon Dangling Bonds in Hydrogenated Amorphous Silicon Nitride Films," J. Appl. Phys. (1995) 77(11):5730-35.

U.S. Appl. No. 13/920,037, filed Jun. 17, 2013, Saxena et al, "Arrays of Integrated Analytical Devices and Methods for Production".

\* cited by examiner

WAVEGUIDE TRANSMISSION

CROSS-REFERENCE TO RELATED APPLICATIONS

This application claims the benefit of U.S. Provisional Application No. 62/107,310, filed Jan. 23, 2015, the full disclosure of which is incorporated herein by reference in its entirety for all purposes.

STATEMENT REGARDING FEDERALLY SPONSORED RESEARCH

Not Applicable.

BACKGROUND OF THE INVENTION

As multiplexed analytical systems continue to be miniaturized in size, expanded in scale, and increased in power, the need to develop improved systems capable of such functionality becomes more important. For example, in optical analyses, increasing multiplex often poses increased difficulties, as it may require more complex optical systems, increased illumination or detection capabilities, and new reaction containment strategies. In some cases, systems seek to increase multiplex by many fold, and even orders of magnitude, which further complicate these considerations. Likewise, in certain cases, the analytical environment for which the systems are to be used is so highly sensitive that variations among different analyses in a given system may not be tolerable. These goals are often at odds with a brute force approach of simply making systems bigger and of higher power, as such steps often give rise to even greater consequences, e.g., inter-reaction cross-talk, decreased signal to noise ratios resulting from either or both of lower signal and higher noise, and the like. It would therefore be desirable to provide analytical systems that have substantially increased multiplex for their desired analyses, and particularly for use in highly sensitive reaction systems, and in many cases, to do so while minimizing negative impacts of such increased multiplex.

Conventional optical systems employ complex optical trains that direct, focus, filter, split, separate, and detect light to and from the sample materials. Such systems typically employ an assortment of different optical elements to direct, modify, and otherwise manipulate light entering and leaving a reaction site. Such systems are typically complex and costly and tend to have significant space requirements. For example, typical systems employ mirrors and prisms in directing light from its source to a desired destination. Additionally, such systems may include light-splitting optics such as beam-splitting prisms to generate two or more beams from a single original beam.

Alternatives to the conventional optical systems have been described, in particular alternative systems having integrated optical components designed and fabricated within highly confined environments. There is, however, a continuing need to increase the performance of analytical systems, and in particular to improve the transmission of optical energy through waveguides, in particular transmitting light in the visible wavelength range.

BRIEF SUMMARY OF THE INVENTION

In some aspects the invention provides a method for increasing the transmission of a waveguide that is prone to develop a resonance grating structure over time during laser illumination comprising: illuminating the waveguide with light from a laser; providing a modulation to the system over time during illumination wherein the modulation results in a change within the waveguide, wherein such change has dimensions greater than the resonance bandwidth of the grating structure that is prone to develop within the waveguide, thereby increasing the transmission through the waveguide over the transmission through the waveguide in the absence of such modulation.

In some cases the modulation comprises modulating the wavelength of light illuminating the waveguide, wherein the range of wavelength modulation is less than 0.2 percent of the center of the range of wavelength modulation. In some cases the modulation comprises modulating the temperature of the waveguide over a temperature range. In some cases the temperature range is from about 3 degrees C. to about 50 degrees C.

In some cases the frequency of modulation is greater than about 0.001 Hz. In some cases the frequency of modulation is between about 1 KHz and 0.01 Hz.

In some cases the wavelength of the light from the laser is from about 450 nm to about 700 nm. In some cases the wavelength of the light from the laser is from about 500 nm to about 650 nm. In some cases the range of wavelength modulation is less than 500 picometers. In some cases the range of wavelength modulation is less than 250 picometers.

In some cases the wavelength modulation is carried out by cycling the laser through two different wavelengths. In some cases the wavelength modulation is carried out by cycling the laser through 5 to 30 different wavelengths. In some cases the wavelength modulation is carried out by randomly addressing wavelengths within the range of wavelength modulation. In some cases the waveguide comprises a SiON core. In some cases the SiON core has a refractive index above about 1.6. In some cases the waveguide comprises a core surrounded by silicon dioxide.

In some cases the waveguide is in a chip. In some cases the chip comprises a silicon chip. In some cases the chip comprises an optical detector. In some cases the optical detector comprises a CMOS detector.

In some aspects the invention provides a system for improved waveguide transmission comprising: a laser providing illumination; and a chip receiving illumination from the laser comprising: at least one waveguide; and a heater in thermal contact with the chip for modulating the temperature of the at least one waveguide over time; wherein the heater periodically modulates the temperature of the chip over time, whereby the transmission through the waveguide is improved over the transmission through the waveguide when the temperature of the chip is not modulated. In some cases the temperature at the chip is modulated over a range of from about 3 degrees C. to about 50 degrees C. In some cases the temperature at the chip is modulated over a range of from about 5 degrees C. to about 20 degrees C.

In some aspects the invention provides a system comprising: a laser providing illumination; and a chip receiving illumination from the laser comprising: at least one waveguide; a coupler for coupling the illumination light into the at least one waveguide; wherein the wavelength of the illumination provided by the laser is modulated over time, wherein the range of wavelength modulation is less than 0.2 percent of the average illumination wavelength.

In some aspects the invention provides a method for providing illumination to a chip comprising at least one waveguide comprising: providing to the chip illumination light from a laser, wherein the wavelength of the illumination provided by the laser is modulated over time, wherein the range of wavelength modulation is less than 0.2 percent of the center of the range of wavelength modulation.

In some cases the range of wavelength modulation is less than 0.1 percent of the average illumination wavelength. In some cases the range of wavelength modulation is less than about 500 picometers. In some cases the range of wavelength modulation is less than about 250 picometers.

In some aspects the invention provides a system for improved waveguide transmission comprising: a laser providing illumination; and a chip receiving illumination from the laser comprising; at least one waveguide; and a coupler for coupling the illumination light into the at least one waveguide; wherein the wavelength of the illumination provided by the laser is modulated over time, wherein the range of wavelength modulation is less than 1 nm.

In some aspects the invention provides a method for providing illumination to a chip comprising at least one waveguide comprising: providing to the chip illumination light from a laser, wherein the wavelength of the illumination provided by the laser is modulated over time, wherein the range of wavelength modulation is less than 1 nm.

In some cases the laser wavelength is between about 450 nm and about 700 nm. In some cases the laser wavelength is between about 500 nm and about 650 nm. In some cases the range of wavelength modulation is less than 500 picometers. In some cases the range of wavelength modulation is less than 250 picometers. In some cases the frequency of wavelength modulation is less than about 1 Hz. In some cases the frequency of wavelength modulation is less than about 0.1 Hz.

In some cases the wavelength modulation is carried out by cycling the laser through more than two different wavelengths. In some cases the wavelength modulation is carried out by cycling the laser through 3 to 30 different wavelengths. In some cases the wavelength modulation is carried out by randomly addressing wavelengths within the range of wavelength modulation. In some cases the wavelength modulation is carried out by monitoring a back reflection level and changing the laser wavelength if the back reflection level exceeds a threshold level. In some cases the threshold level is between 0.1% and 2% of the intensity of complete back reflection. In some cases the back reflection level is determined by measuring a drop in forward transmission.

In some cases the waveguide comprises a SiON core. In some cases the waveguide comprises a core that is surrounded by silicon dioxide. In some cases the chip comprises a sensor. In some cases the sensor comprises a CMOS sensor. In some cases the waveguides provide illumination to nanoscale wells on the chip comprising fluorescent species.

In some aspects the invention provides a method for illuminating a semiconductor waveguide that exhibits time-dependent back reflection comprising; illuminating the semiconductor waveguide with a laser, wherein the wavelength of the illumination provided by the laser is modulated over time, wherein the range of wavelength modulation is less than 0.2 percent of the average illumination wavelength, thereby reducing or eliminating the time-dependent back reflection.

In some aspects the invention provides a method for producing a Bragg grating within an optical waveguide comprising: providing a SiON waveguide having a refractive index above 1.6; irradiating the waveguide with a writing beam having a periodic intensity corresponding to the desired grating for a period of time sufficient to form a grating within the waveguide.

In some cases the irradiation is provided within the waveguide. In some cases the irradiation is provided external to the waveguide. In some cases the periodic intensity comprises a standing wave. In some cases the periodic intensity is provided by interference between two or more beams.

In some cases the wavelength of the writing beam is from 450 nm to about 700 nm.

In some cases the method further comprises erasing the Bragg grating that is formed by irradiation the waveguide with a second writing beam having a periodic intensity different than that of the writing beam used to form the Bragg grating.

In some cases in addition to erasing the initial Bragg grating, the second writing beam produces a second Bragg grating having a different Bragg wavelength.

DETAILED DESCRIPTION OF THE INVENTION

General

Figure 1A:
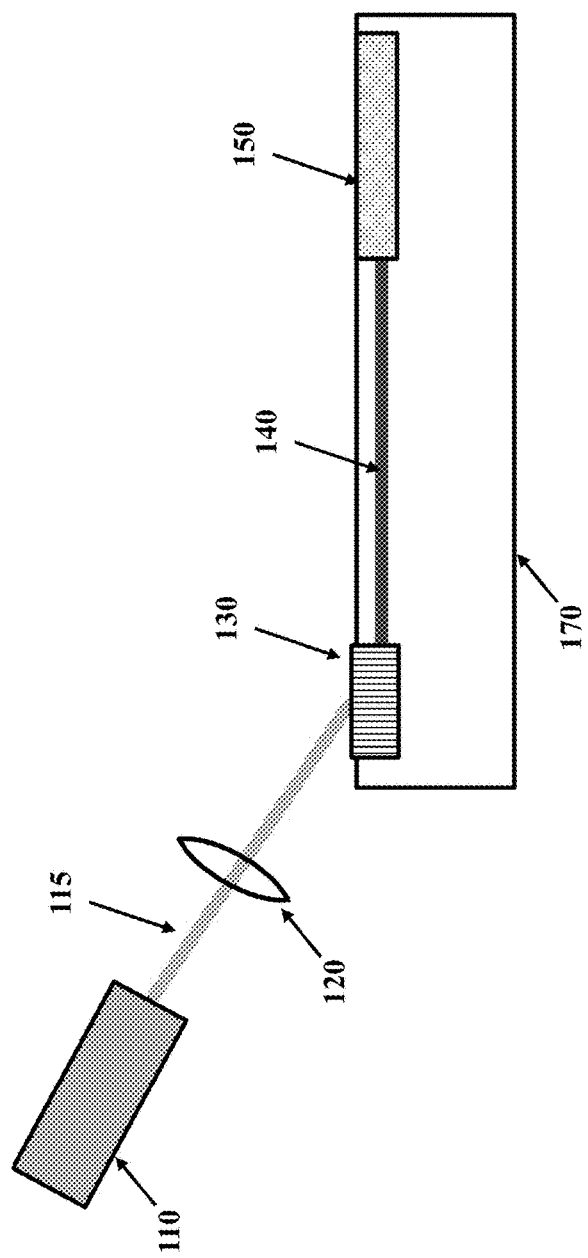
FIG. 1A shows a system, apparatus, or portion of an apparatus for the invention.

In some aspects, the present invention provides methods, instruments, systems, and devices for improved transmission of light through waveguides. Some waveguides will exhibit back reflection that is variable over time when illuminated with a single wavelength, for example, with a laser. This can happen, for example, with SiON waveguides illuminated with laser light in the visible wavelength range. This backs reflection can be undesirable as it decreases the amount of light delivered by the waveguide. In addition, this back reflection can be undesirable because it can cause other problems such as being transmitted back into the laser, creating instability and laser damage.

We have found that this back reflection can be significantly reduced or eliminated by illuminating the waveguide with light having a wavelength that is modulated in time. We have found that an effective amount of modulation of the wavelength can be very small, for example, less than about 500 pm (0.5 nm) for an average illumination wavelength of about 500 nm.

In addition, we have found that we can significantly reduce or eliminate the back reflection in the waveguide by raising the temperature of the waveguide.

While not being bound by theory, it is believed that time dependent back reflection can be caused by the formation within the waveguide of a Bragg grating by the illumination light. That is, the illumination light from a laser with a fixed wavelength "writes" a grating into the waveguide at a spacing corresponding to the wavelength of the light. The grating with this spacing will then cause the backward reflection of some of the light passing through the waveguide. In some cases, the backward reflected light is believed to further intensify the grating, resulting in even more back reflected light. In addition, we have seen evidence that a grating which is "written" into the waveguide as described above can be erased by exposure to illumination light at a different wavelength than the wavelength at which it was formed.

It is believed that by modulating the frequency of the illumination light, we are able to inhibit the formation of the grating by not allowing sufficient time for it to form, and that in addition, by moving to a different wavelength, any grating that may have begun to have formed will be erased by illumination with the different wavelength light.

The approaches described herein can be used with any suitable waveguide that exhibits this time-dependent back reflection phenomenon. The approaches can be used for instance, with chips described herein for analysis where the waveguides provide illumination light to wells for fluorescence measurements of samples within the wells. The approaches described herein can also be used with other waveguides on chips, such as with PLCs or FSCs.

Other aspects of the invention provide methods of statically and dynamically creating waveguide Bragg gratings. We have found that we can write Bragg gratings within SiON waveguides using light in the visible range. The Bragg gratings can be formed by exposure to a standing wave of laser light in the visible range. We have also shown that the gratings formed in this manner can be erased, for example by exposure to standing waves of laser light. The laser light used for erasing can have a wavelength that is only slightly different in wavelength than the light of the original writing beam. For example, difference in wavelength between the writing and reading laser light can be less than 0.1 percent or less than 0.01 percent. In some cases the erasing light is at least greater than the resonance bandwidth for the Bragg grating. In some cases the erasing light is different from the writing light by greater than about 15 picometers, greater than about 20 picometers, greater than about 25 picometers, greater than about 30 picometers, or greater about than 50 picometers. In some cases, erasure is accomplished by providing laser light that has its wavelength modulated over time as described herein.

The invention can be useful in improving the effectiveness of any type of device that carries light via waveguides. It can be useful for devices that contain waveguides that transmit light in the visible range, for example, that transmit light from about 450 nm to about 700 nm. It can be useful for waveguides formed on semiconductor chips, such as Silicon chips, and in particular such waveguides having a SiON core. Examples are analytical devices that measure levels of fluorescence for which the waveguides provide excitation illumination in the visible range, and PLC devices used in the visible range.

Improving Transmission with Modulation of Wavelength or Waveguide Temperature

FIG. 1A shows a system, apparatus, or portion of an apparatus for the invention. A laser 110 sends light 115 to a chip 170. In some cases optical element or elements 120 are used to shape, steer, or otherwise control the properties of the laser as it reaches the chip 170. The laser light enters the waveguide 140. The light is transmitted through the waveguide 140 to the area of interest 150 on the chip 170. Here, a coupler is used to direct the laser light through space into the chip through a coupler 130, which can be, for example, a grating coupler. While a grating coupler is shown, it is to be understood that any type of coupler, prism, or other interface optical element can be used to direct the laser light into the fiber.

It is typically desired that the waveguide have high levels of light transmission, that is, low levels of light loss as it transmits the light to the region of interest 150. In some cases, the waveguide will exhibit a time dependent back reflection when continuously illuminated with light of a fixed wavelength from the laser. We have seen that this back reflection can be significant, in some cases resulting in greater than 90% loss of the light. Even when the light loss is less than this, it can be a problem, both in terms of raising the requirement for illumination power for a given level of delivered light, and in terms of deleterious effects of the re-directed light. As described herein in more detail, we believe that the laser light in the waveguide is able to form a Bragg grating within the waveguide under some conditions, and that this Bragg grating can cause the reflection of light at the same wavelength that the grating was formed.

We have found that we can reduce or eliminate this back reflection by providing a modulation to the system over time during illumination where the modulation results in a change within the waveguide, and where such change has dimensions greater than the resonance bandwidth of the grating structure that is prone to develop within the waveguide.

In particular, we have found that we can reduce or eliminate the back reflection by modulating the wavelength of the illumination over time during illumination. We have found that we can either prevent the buildup of back reflection or can eliminate (erase) the back reflection by fairly small modulations in the wavelength of light. The light modulation can be, for example, less than 0.2 percent, less than 0.1 percent, or less than 0.001 percent of the center of wavelength modulation range. The light modulation can be, for example, less than about 1 nm, less than about 500 picometers, less than about 200 picometers, less than about 100 picometers, or less than about 50 picometers. The light modulation can be, for example from about 15 picometers to about 500 picometers, or from about 30 picometers to about 200 picometers.

Being able to accomplish the increase in transmission through the waveguide with such a small variation in wavelength is very useful because in some cases, it allows the light delivered to the desired region to be effectively the same over time from the perspective of the application. For example, where the application is fluorescent analysis, and the light through the waveguide is excitation light, the fluorescent analysis is indifferent as to whether the wavelength of light has changed by this small amount. Another advantage is the ease of implementing this modulation in a laser system. Modulations of wavelength on this order can be obtained with a laser, for example by simply changing the temperature within the laser, for example by slightly changing the dimensions of the laser cavity. While one might be able to improve the transmission through the waveguide by using larger ranges of wavelength modulation, larger changes can be more difficult and more costly to implement.

The modulation of wavelength can be done at the laser, or can be accomplished by using optical elements 120 between the laser 110 and the waveguide 140. The frequency of modulation can depend on the time it takes for the back reflection to develop in the waveguide. We have found that in some cases, wavelength modulation frequencies on the order of 0.001 can be effective. Wavelength modulations with frequencies above 1 KHz can also be used. One of skill in the art will find that there are frequencies that become impractical for a given laser and illumination optics.

The wavelength can be modulated in any suitable manner. In some cases, there are two set points for wavelength, and the wavelength is periodically cycled between the two wavelengths. In some cases, there are more than two specific wavelengths within the range that are applied. For example, in some cases from 2 to 200 levels or from 3 to 100 levels or from 3 to 30 levels are applied. In some cases the discrete levels are repeatedly revisited in cycles, in some cases, wavelength levels within the range are randomly applied. In some cases, rather than specific wavelength levels, the wavelength is varied as a function such as a smooth function. The form of the modulation can be any suitable form including a sine wave, a sawtooth, or a square wave function. In some cases the laser wavelength can be dithered over the range of modulation.

The dwell time at each wavelength can be, for example, from between 0.1 second to 100 seconds or from between 1 second and 30 seconds.

Where there is a periodic wave function the period is typically between about 10 seconds and about 200 seconds.

The wavelength steps are designed to be large enough to move off any incipient Bragg reflection condition. The wavelength steps can be, for example, from about 15 picometers to about 500 picometers.

In some cases the laser emission is briefly extinguished while making a change in laser wavelength. We have found that if the time that the laser is extinguished is short enough, this is not a problem for use in exciting fluorophores. For example the time can be limited to a very fraction of the fluorescence detection integration time or a fraction of the camera frame time. Thus the power toggling does not substantially disturb the fluorescence signaling.

In some cases it is desirable to have a wave function that provides a relatively long time between revisiting a wavelength that was previously used. One useful wave function to accomplish this objective is a sawtooth pattern in which a series of wavelengths are visited from low to high wavelength, then the wavelength is dropped back to the original low wavelength. A reverse sawtooth function stepping from low to high, and then returning to the high level can also be used. A sawtooth function with from 3 to 30 steps can be useful.

In some cases, active wavelength control is used. In an active control approach the optics constantly monitor any Bragg reflection. The laser is held at a constant wavelength until a Bragg reflection is detected. At that point a new wavelength is commanded. In some cases, this approach will result in increased laser lifetime over the fixed function mode. Making fewer wavelength steps over time can reduce wear and tear on the laser. It can also be useful for minimizing power transients that could effect the stability of the fluorescence signal.

As an example, the system triggers a change in wavelength when the strength of the Bragg reflection first exceeds a threshold level, for example from 0.1% to about 5% of full reflection intensity, or about 0.5% to about 2% of the full reflection intensity. The wavelength would be incremented, for example, by about 15 picometers to about 500 picometers, or by about 30 picometers to about 100 picometers. The system would then remain at the new wavelength until a Bragg reflection again exceeds the threshold level. The pattern of wavelengths visited could follow any suitable function, similar to those described for the fixed wavelength patterns. For example, the system can ramp up at each event, and then wrap around to a shorter wavelength after reaching the end of the specified wavelength range, i.e., the highest desired wavelength.

There are some practical considerations for the choice of the reflection value at which to trigger the move to a new wavelength. One wishes to trigger at a low reflection value to order to arrest a possible runaway situation in which a substantial Bragg reflection quickly feeds on itself to produce a stronger reflection. This demands the use of a low reflection threshold. However, noise in the reflection detection system sets a practical lower limit to the threshold. We have found that a range of about 0.1% to about 5% or 0.5% to about 2% is a useful range.

For active wavelength control there are various methods that can be used to measure the back reflection for triggering a wavelength change. This can be done, for example, with light sensors on the illuminated chip itself. It can also be done in free space with optical hardware mounted external to the chip. In some cases, on-chip structures such as splitter trees designed for the forward-going laser light do not necessarily efficiently transmit reflected light. To account for this, a structure dedicated to monitoring back reflection, such as a waveguide splitter that taps a small amount of backward going power can be used.

Instead of monitoring the back reflection directly, in some cases, the back reflection can be monitored by observing a drop in forward transmission. In this approach the laser wavelength is incremented when the light intensity transmitted through the waveguide, e.g. reaching the active portion of the sequencing, chip dropped below a set threshold.

The waveguide can be any suitable waveguide including a fiber, a planar waveguide, or a channel waveguide. The waveguide can be single mode or multi-mode waveguides, as these sorts of gratings can be used to manage the distribution of power in different transverse mode (even to couple them to radiation modes for detection in free space). The applications are routing (mode to mode), wavelength selection/spectral shaping, input/output coupling. One reason to consider using such a technique is that etching gratings on this scale requires very high end fab equipment, whereas making an interference pattern of the desired scale requires substantially less costly equipment. Also, this process can more straightforwardly making sinusoidal gratings (wrt etching), a type of grating which is often preferred for making a very precise mode selection (to reflect a very narrow spectral band, but transmit all others similar to an add/drop filter in telecom).

The waveguide 140 is shown as being on a chip 170, which can be a semiconductor chip, for example, a silicon chip. Particular systems of interest with respect to the invention are SiON waveguides, for example formed on silicon chips. The SiON waveguide will have a core of SiON, and is typically surrounded by a cladding material of lower refractive index such as silicon dioxide. As is known in the art, SiON can be formed in a deposition process, and the ratio of the elements can be adjusted to control the properties. For example, the ratio of Oxygen to Nitrogen can be varied in order to change the refractive index of the film. For the SiON waveguides of the invention, the composition is often controlled to have a refractive index greater than about 1.6, greater than about 1.7, or greater than about 1.8. The refractive index can be measured, for example, at the sodium D line.

We have found that another approach to reduce or eliminate back reflections and thereby improve waveguide transmission is to modulate the temperature of the waveguide. This method does not require the laser wavelength to be modulated over time, however, in some cases the two approaches can be used together. Any suitable means can be employed for modulating the temperature of the waveguide. For example, a heating element or heating/cooling element can be brought into thermal contact with the waveguide. Where the waveguide is in a chip, the heating element or heating/cooling element can be in physical contact with the chip 170. Radiation methods such as infrared illumination can also be used.

There are various methods for applying heat in order to improve transmission through the waveguide. In the simplest case, one can run the chip at a fixed temperature with a fixed wavelength laser for a period of time during which, even if a back reflection begins to form, the level of loss is acceptable. Then the waveguide is brought to a different temperature, e.g. 5 degrees different than the previous waveguide temperature. In some cases this will produce a large enough change within the waveguide such that little or no back reflection will be seen.

For example, in carrying out an analysis, the analysis may take 1 hour to complete, during which time a back reflection of 2% is formed. If this level of transmission loss is acceptable, then prior to the next analysis, the temperature of the chip is set to a new temperature for the duration of the second analysis, and so on. The same approach can be taken with wavelength modulation, simply varying at a time period that corresponds with use.

Another approach to modulating the temperature or the wavelength to reduce or eliminate back reflection is to use a measurement of reflection or transmission over time to set the modulation. For example, a feedback loop is set up in which, when the back reflection or loss in transmission reaches a certain value, the temperature or wavelength is changed to a new value.

In many cases it is desirable to just carry out the modulation over a given known frequency as described herein, either by cycling specific values, randomly hitting values within a range, or modulating the wavelength or temperature over the range through a function.

The intensity of the illumination light can be adjusted in order to control the rate of appearance and of removal of the back reflection. In some cases light of greater than 1 mW, greater than 2 mW, greater than 5 mW, greater than 10 mW or greater than 20 mW is used.

Figure 1B:
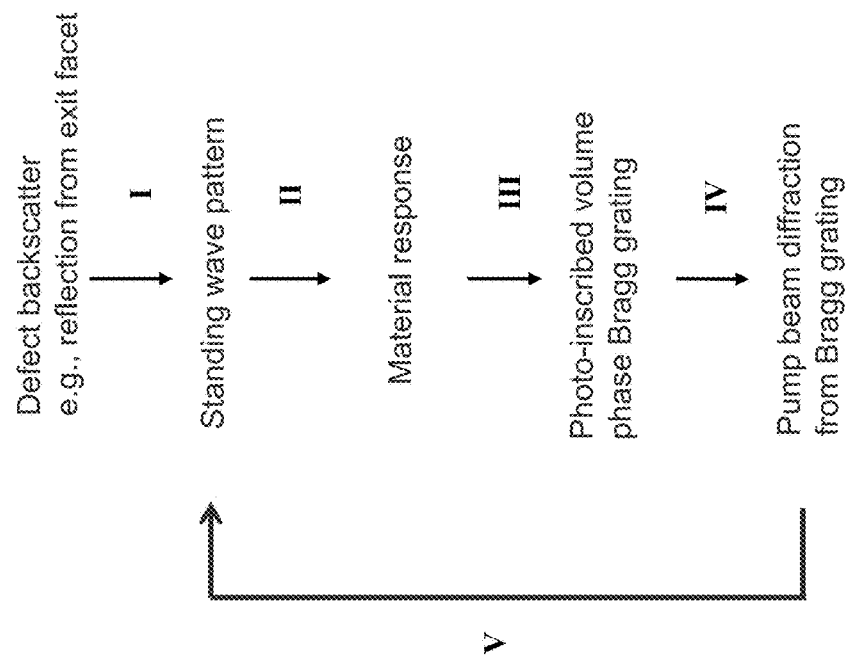
FIG. 1B shows a flow chart outlining a proposed mechanism for the time dependent back reflection.

FIG. 1B shows a flow chart outlining a proposed mechanism for the time dependent back reflection. It is believed that a standing wave pattern is formed within the waveguide (step I). The standing wave pattern can be formed, for example, but backscatter from a defect or reflection from a portion of the waveguide routing pattern such as an exit facet. In step II there is a material response, for example at $m*hc/l$, & L such as a 2-photon absorption that affects UV color centers. The UV absorption change can then result in a change in the refractive index at the illumination wavelength. This change results in a photo-inscribed volume phase Bragg grating (step III). The Bragg grating results in even more of the light sent back (step IV). The increased backward traveling light intensifies the standing wave pattern (step V). As can be seen, this step feeds back, in a manner in which the initial grating can become more and more effective, sending back a higher and higher proportion of the light. This mechanism is consistent with our observations of the time dependent back reflection. A similar mechanism can then also be invoked to understand the mechanism for erasing or detuning the grating by modulating the wavelength of the illumination light or the temperature of the waveguide. At a new wavelength, the old grating will be ineffective, and to the extent that a new grating is written, it can tend to erase the previous grating. Analogously, a change in temperature can change, the properties of the waveguide such that the original wavelength no longer corresponds to the period of the original grating. The changes in the properties of the waveguide can be changes in dimension, changes in refractive index, or changes in absorption.

Producing a Static or Dynamic Waveguide Bragg Grating

In some aspects, the invention provides a method of producing a grating within a waveguide. The grating that is produced can be either static (for example written at one, lower wavelength, and utilized at a higher wavelength), or dynamic, such that the grating can be written, erased, and written again. Each time it is written can be with a different set of wavelengths.

Figure 2:
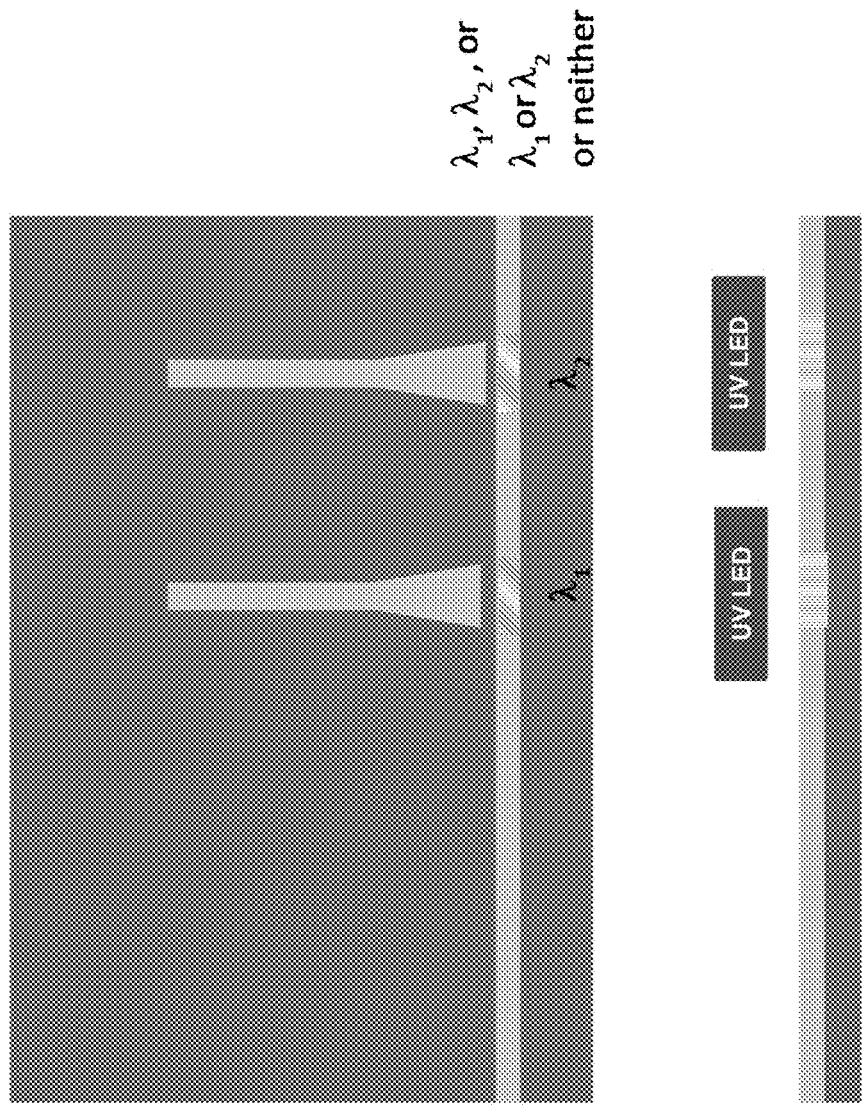
FIG. 2 shows an example of a dynamic grating written externally.

In one aspect the method uses a waveguide having a SiON core where the SiON has a refractive index grating above about 1.6, above about 1.7 or above about 1.8. The light used to produce the gratings can be in the visible, for example from 450 nm to 700 nm. The light could also be below 450 in some cases. In many cases, the gratings are formed by light that is at a higher wavelength than would normally be considered for writing such gratings. We believe that the The gratings can be written internally in the waveguide by the mechanisms and structures described above. In addition, the gratings can be written by providing the light required for writing externally. Dynamic gratings require a path for irradiance in the UV to erase the grating previously formed (presumably by an external writing method). One formulation of that would be to have two routing paths for which one could make a decision subsequently. Note that longer period gratings could be used to couple light between polarization states, or transverse modes (or output couple to a radiation mode). FIG. 2 shows an example of a dynamic grating written externally.

With more complexity, this could be writing a grating rather than erasing a grating. Note that the erasure may also be partial, if one wished to use this as a controlled splitter, or an equalizer. As telecom has the distinct advantage of having amplifiers, even a weak signal can be useful in distributing signals. Note that for a known pair of wavelengths, one can make a fan in geometry as well as the fan out shown in FIG. 2.

Waveguide Addressed Analytical Systems

In some aspects the present invention is directed to improved systems, devices and methods for performing analytical operations, and particularly optical analysis of chemical, biochemical and biological reactions for use in chemical, biological, medical and other research and diagnostic applications. The systems, devices and methods of the invention are particularly suited for application in integrated analytical components, e.g., where multiple functional components of the overall analysis system are co-integrated within a single modular component. However, as will be clear upon reading the following disclosure, a number of aspects of the invention will have broad utility outside of such integrated devices and systems.

In general, the optical analyses that are subject of the present invention, seek to gather and detect one or more optical signals from a reaction of interest, the appearance or disappearance of which, or localization of which, is indicative of a given chemical or biological reaction and/or the presence or absence of a given substance within a sample material. In some cases, the reactants, their products, or substance of interest (all of which are referred to as reactants herein) inherently present an optically detectable signal which can be detected. In other cases, reactants are provided with exogenous labeling groups to facilitate their detection.

Nucleic Acid Sequencing

In a number of different nucleic acid sequencing analyses, fluorescently labeled nucleotides are used to monitor the polymerase-mediated, template-dependent incorporation of nucleotides in a primer extension reaction. In particular, a labeled nucleotide is introduced to a primer template polymerase complex, and incorporation of the labeled nucleotide is detected. If a particular type of nucleotide is incorporated at a given position, it is indicative of the underlying and complementary nucleotide in the sequence of the template molecule. In traditional Sanger sequencing processes, the detection of incorporation of labeled nucleotides utilizes a termination reaction where the labeled nucleotides carry a terminating group that blocks further extension of the primer. By mixing the labeled terminated nucleotides with unlabeled native nucleotides, one generates nested sets of fragments that terminate at different nucleotides. These fragments are then separated by capillary electrophoresis, to separate those fragments that differ by a single nucleotide, and the labels for the fragments are read in order of increasing fragment size to provide the sequence (as provided by the last added, labeled terminated nucleotide). By providing a different fluorescent label on each of the types of nucleotides that are added, one can readily differentiate the different nucleotides in the sequence (e.g., U.S. Pat. No. 5,821,058, incorporated herein for all purposes by this reference).

In newer generation sequencing technologies, arrays of primer-template complexes are immobilized on surfaces of substrates such that individual molecules or individual and homogeneous groups of molecules are spatially discrete from other individual molecules or groups of molecules, respectively. Labeled nucleotides are added in a manner that results in a single nucleotide being added to each individual molecule or group of molecules. Following the addition of the nucleotide, the labeled addition is detected and identified.

In some cases, the processes utilize the addition of a single type of nucleotide at a time, followed by a washing step. The labeled nucleotides that are added are then detected, their labels removed, and the process repeated with a different nucleotide type. Sequences of individual template sequences are determined by the order of appearance of the labels at given locations on the substrate.

In other similar cases, the immobilized complexes are contacted with all four types of labeled nucleotides where each type bears a distinguishable fluorescent label and a terminator group that prevents the addition of more than one nucleotide in a given step. Following the single incorporation in each individual template sequence (or group of template sequences,) the unbound nucleotides are washed away, and the immobilized complexes are scanned to identify which nucleotide was added at each location. Repeating the process yields sequence information of each of the template sequences. In other cases, more than four types of labeled nucleotides are utilized.

In particularly elegant approaches, labeled nucleotides are detected during the incorporation process, in real time, by individual molecular complexes. Such methods are described, for example, in U.S. Pat. No. 7,056,661, which is incorporated herein by reference in its entirety for all purposes. In these processes, nucleotides are labeled on a terminal phosphate group that is released during the incorporation process, so as to avoid accumulation of label on the extension product, and avoid any need for label removal processes that can be deleterious to the complexes. Primer/template polymerase complexes are observed during the polymerization process, and nucleotides being added are detected by virtue of their associated labels. In one particular aspect, they are observed using an optically confined structure, such as a zero mode waveguide (See, e.g., U.S. Pat. No. 6,917,726, which is incorporated herein by reference in its entirety for all purposes) that limits exposure of the excitation radiation to the volume immediately surrounding an individual complex. As a result, only labeled nucleotides that are retained by the polymerase during the process of being incorporated are exposed to excitation illumination for a time that is sufficient to identify the nucleotide. In another approach, the label on the nucleotide is configured to interact with a complementary group on or near the complex, e.g., attached to the polymerase, where the interaction provides a unique signal. For example, a polymerase may be provided with a donor fluorophore that is excited at a first wavelength and emits at a second wavelength, while the nucleotide to be added is labeled with a fluorophore that is excited at the second wavelength, but emits at a third wavelength (See, e.g., U.S. Pat. No. 7,056,661, previously incorporated herein). As a result, when the nucleotide and polymerase are sufficiently proximal to each other to permit energy transfer from the donor fluorophore to the label on the nucleotide, a distinctive signal is produced. Again, in these cases, the various types of nucleotides are provided with distinctive fluorescent labels that permit their identification by the spectral or other fluorescent signature of their labels.

In the various exemplary processes described above, detection of a signal event from a reaction region is indicative that a reaction has occurred. Further, with respect to many of the above processes, identification of the nature of the reaction, e.g., which nucleotide was added in a primer extension reaction at a given time or that is complementary to a given position in a template molecule, is also achieved by distinguishing the spectral characteristics of the signal event.

The optical paths of the overall systems of the invention serve one or more roles of delivering excitation radiation to the reaction region, e.g., to excite fluorescent labeling molecules that then emit the relevant optical signal, conveying the optical signal emitted from the reaction region to the detector, and, for multispectral signals, i.e., multiple signals that may be distinguished by their emission spectrum, separating those signals so that they may be differentially detected, e.g., by directing different signals to different detectors or different locations on the same detector array. The differentially detected signals are then correlated with both the occurrence of the reaction, e.g., a nucleotide was added at a given position, and the determination of the nature of the reaction, e.g., the added nucleotide is identified as a particular nucleotide type, such as adenosine.

In conventional analytical systems, the optical trains used to deliver excitation light to the reaction regions, and convey optical signals from the reaction regions to the detector(s) can impart size, complexity and cost aspects to the overall system that would preferably be reduced. For example, such optical trains may include collections of lenses, dispersion elements, beam splitters, beam expanders, collimators, spatial and spectral filters and dichroics, that are all assembled to deliver targeted and uniform illumination profiles to the different reactions regions. In large scale systems, these components must be fabricated, assembled, and adjusted to ensure proper alignment, focus, and isolation from other light and vibration sources to optimize the transmission of excitation light to the reaction regions. As the number of addressed reaction regions, or the sensitivity of the system to variations in excitation light intensity is increased, addressing these and other issues becomes more important, and again typically involves the inclusion of additional componentry to the optical train, e.g., alignment and focusing mechanisms, isolation structures, and the like.

With respect to the collection and detection of optical signals, conventional systems typically employ optical trains that gather emitted optical signals from the reaction region, e.g., through an objective lens system, transmit the various different signals through one or more filter levels, typically configured from one or more dichroic mirrors that differentially transmit and reflect light of different wavelengths, in order to direct spectrally different optical signals to different detectors or regions on a given detector. These separated optical signals are then detected and used to identify the nature of the reaction that gave rise to such signals. As will be appreciated, the use for such differential direction optics imparts substantial space, size and cost requirements on the overall system, in the form of multiple detectors, multiple lens and filter systems, and in many cases complex alignment and correlation issues. Many of these difficulties are further accentuated where the optical trains share one or more sub-paths with the excitation illumination, as signal processing will include the further requirement of separating out excitation illumination from each of the detected signals.

Again, as with the excitation optical train, above, as the sensitivity and multiplex of the system is increased, it increases the issues that must be addressed in these systems, adding to the complexity of already complex optical systems. Further, the greater the number of optical components in the optical train, the greater the risk of introducing unwanted perturbations into that train and the resulting ability to detect signal. For example, optical aberrations in optical elements yield additional difficulties in signal detection, as do optical elements that may inject some level of autofluorescence into the optical train, which then must be distinguished from the signaling events.

Integrated Devices

The present invention is directed, in part, to systems, devices and methods that utilize the waveguide illumination devices and methods described herein within integrated detection and optical path components in small scale devices that optionally also include one or more of the reaction regions themselves, fluidic components for the reaction of interest, and excitation illumination paths and optionally excitation illumination sources. Integration of some or all of above described components into a single, miniaturized device addresses many of the problems facing larger, non-integrated analytical systems, such as size, cost, weight, inefficiencies associated with long path or free space optics, and the like. For example, highly multiplexed analytical systems comprising integrated waveguides for the illumination of nanoscale samples are described in U.S. Patent Application Publication Nos. 2008/0128627 and 2012/0085894 Further optical systems for the analysis of nanoscale samples, including the illumination and detection of such samples, are described in U.S. Patent Application Publication Nos. 2012/0014837, 2012/0021525, and 2012 0019828. Additional nanoscale illuminations systems for highly multiplexed analysis are described in U.S. Patent Application Publication Nos. 2014/0199016 and 2014/0287964.

Other examples of such integrated systems are described, for example, in U.S. Published Patent Application Nos. 2012/0014837, 2012/0019828, and 2012/0021525, and Provisional Patent No. 61/738,637, filed Dec. 18, 2012, the entire contents of each of which are incorporated herein by reference in their entirety for all purposes. By integrating the detection elements with the reaction regions, either directly or as a coupled part, one can eliminate the need for many of the various components required for free space optics systems, such as much of the conveying optics, lenses, mirrors, etc., as well as, among other things, various alignment functionalities, as alignment is achieved through integration. The present invention seeks to further improve the benefits afforded by such devices by simplifying, to a greater extent, the optical components of the analytical devices, further reducing the cost and complexity of such devices and improving available signal in the process.

The analytical system in accordance with the present invention employs one or more analytical devices. In an exemplary embodiment, the system includes an array of analytical devices formed as a single integrated device. The exemplary array is configured for single use as a consumable. In various embodiments, the integrated optical element includes other components including, but not limited to local fluidics, electrical connections, a power source, illumination elements, a detector, logic, and a processing circuit. Each analytical device or array is configured for performing an analytical operation as described above.

Figure 3:
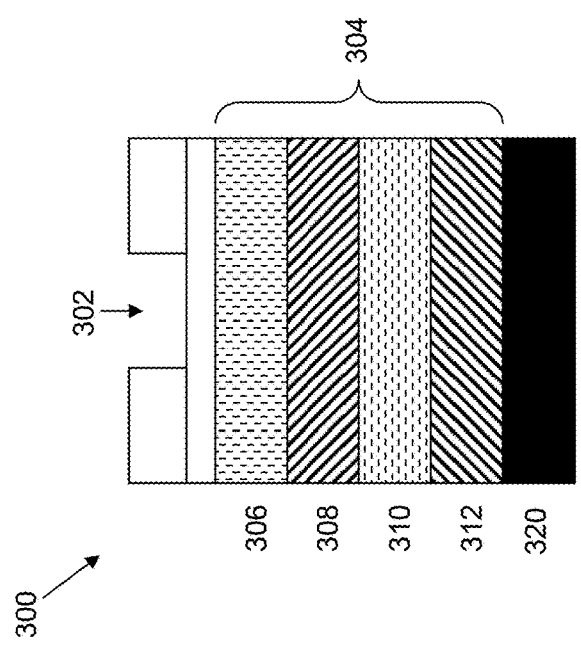
FIG. 3 shows a block diagram of an integrated analytical device.

While the components of each device and the configuration of the devices in the system may vary, each analytical device can comprise, at least in part, the general structure shown as a block diagram in FIG. 3. As shown, an analytical device 300 typically includes a reaction cell 302, in which the reactants are disposed and from which the optical signals emanate. "Reaction cell" is to be understood as generally used in the analytical and chemical arts and refers to the location where the reaction of interest is occurring. Thus, "reaction cell" may include a fully self-contained reaction well, vessel, flow cell, chamber, or the like, e.g., enclosed by one or more structural barriers, walls, lids, etc., or it may comprise a particular region on a substrate and/or within a given reaction well, vessel, flow cell or the like, e.g., without structural confinement or containment between adjacent reaction cells. The reaction cell may include structural elements to enhance the reaction or its analysis, such as optical confinement structures, nanowells, posts, surface treatments, such as hydrophobic or hydrophilic regions, binding regions, or the like.

In various respects, "analytical device" refers to a reaction cell and associated components that are functionally connected. In various respects, "analytical system" refers to one or more associated analytical devices and associated components. In various respects, "analytical system" refers to the larger system including the analytical system and other instruments for performing an analysis operation. For example, in some cases, the analytical devices of the invention are part of an analytical instrument or analytical system.

The analytical device can be removably coupled into the instrument. Reagents can be brought into contact with the analytical device before or after the analytical device is coupled with the system. The system can provide electrical signals and/or illumination light to the analytical device, and can receive electrical signals from the detectors in the analytical device. The instrument or system can have computers to manipulate, store, and analyze the data from the device. For example, the instrument can have the capability of identifying and sequences of added nucleotide analogs for performing nucleic acid sequencing. The identification can be carried out, for example, as described in U.S. Pat. No. 8,182,993, which is incorporated herein by reference for all purposes.

In some cases, one or more reactants for the reaction of interest may be immobilized, entrained or otherwise localized within a given reaction cell. A wide variety of techniques are available for localization and/or immobilization of reactants, including surface immobilization through covalent or non-covalent attachment, bead or particle based immobilization, followed by localization of the bead or particle, entrainment in a matrix at a given location, and the like. Reaction cells may include ensembles of molecules, such as solutions, or patches of molecules, or it may include individual molecular reaction complexes, e.g., one molecule of each molecule involved in the reaction of interest as a complex. Similarly, the overall devices and systems of the invention may include individual reaction cells or may comprise collections, arrays or other groupings of reaction cells in an integrated structure, e.g., a multiwall or multi-cell plate, chip, substrate or system. Some examples of such arrayed reaction cells include nucleic acid array chips, e.g., GeneChip® arrays (Affymetrix, Inc.), zero mode waveguide arrays (as described elsewhere herein), microwell and nanowell plates, multichannel microfluidic devices, e.g., LabChip® devices (Caliper Life Sciences, Inc.), and any of a variety of other reaction cells. In various respects, the "reaction cell", sequencing layer, and zero mode waveguides are similar to those described in U.S. Pat. No. 7,486,865 to Foquet et al., the entire contents of which are incorporated herein for all purposes by this reference. In some cases, these arrayed devices may share optical components within a single integrated overall device, e.g., a single waveguide layer to deliver excitation light to each reaction region. Approaches to illuminating analytical devices with waveguides are provided in U.S. Pat. Nos. 8,207,509, and 8,274,040 which are incorporated herein by reference for all purposes.

Although an analytical device may include an array of analytical devices having a single waveguide layer and reaction cell layer, one will appreciate that a wide variety of layer compositions may be employed in the waveguide array substrate and cladding/reaction cell layer and still achieve the goals of the invention (see, e.g., published U.S. Pat. No. 7,820,983, incorporated herein for all purposes by reference).

The analysis system typically includes one or more analytical devices 300 as illustrated in FIG. 3 having a detector element 320, which is disposed in optical communication with the reaction cell 302. Optical communication between the reaction cell 302 and the detector element 320 may be provided by an optical train 304 comprised of one or more optical elements generally designated 306, 308, 310 and 312 for efficiently directing the signal from the reaction cell 302 to the detector 320. These optical elements may generally comprise any number of elements, such as lenses, filters, gratings, mirrors, prisms, refractive material, or the like, or various combinations of these, depending upon the specifics of the application. In addition to components for directing the optical signal from the reaction region to the detector, the chip can also have optical components for delivering illumination light to the reaction regions for performing fluorescent measurements.

In various embodiments, the reaction cell 302 and detector element 320 are provided along with one or more optical elements in an integrated device structure. By integrating these elements into a single device architecture, one improves the efficiency of the optical coupling between the reaction cell and the detector. As used herein, the term integrated, when referring to different components of an analytical device typically refers to two or more components that are coupled to each other so as to be immobile relative to each other. As such, integrated components may be irreversibly or permanently integrated, meaning that separation would damage or destroy one or both elements, or they may be removably integrated, where one component may be detached from the other component, provided that when they are integrated, they are maintained substantially immobile relative to one another. In some cases, the components are integrated together in one chip. In some cases, the detector portion is part of a separate instrument, and the reaction cell component is part of a chip. In the case where the reaction cell component is in a chip separate from the detector component, optical element components for directing the optical signal from the reaction cell to the detector can be in either the reaction cell component chip, in the detector component, or a combination in which some components are in the reaction cell component chip and others are in the detector.

For the devices, methods and systems of the invention, even where the detector is part of an instrument and separate from the reaction cell component chip, the chip will typically be placed directly onto the detector with a minimal open space between the reaction cell chip and the detector. In some cases, the space between the reaction cell chip and the detector will be less than 1 micron, less than 10 microns, less than 100 microns, or less than a millimeter.

The chip will typically have alignment structures to allow for the precise alignment of the reaction cells with the portions of the detector to which they correspond.

Where the reaction cell component, optical components, and detector are irreversibly or permanently integrated into a chip, such a chip can be produced by fabrication in a monolithic form, or two or more of the components can be manufactured separately and connected together to form the chip. The connection between the chip components can be accomplished by any suitable method including adhesion and wafer bonding.

The choice of whether to have all of the components integrated into a chip or to have the detector component separately associated with the instrument can be made depending on the application. A permanently integrated chip approach has the advantage that the detector can be manufactured in intimate contact with the reaction cell and other components under controlled conditions allowing for precise registration. The approach in which the detector is not integrated into the reaction cell chip, but is part of the instrument has the advantage that the detector can be used over and over again with different reaction cell chips.

In conventional optical analysis systems, discrete reaction vessels are typically placed into optical instruments that utilize free-space optics to convey the optical signals to and from the reaction vessel and to the detector. These free space optics tend to include higher mass and volume components, and have free space interfaces that contribute to a number of weaknesses for such systems. For example, such systems have a propensity for greater losses given the introduction of unwanted leakage paths from these higher mass components, and typically introduce higher levels of auto-fluorescence, all of which reduce the signal to noise ratio (SNR) of the system and reduce its overall sensitivity, which, in turn can impact the speed and throughput of the system. Additionally, in multiplexed applications, signals from multiple reaction regions (i.e., multiple reaction cells, or multiple reaction locations within individual cells), are typically passed through a common optical train, or common portions of an optical train, using the full volume of the optical elements in that train to be imaged onto the detector plane. As a result, the presence of optical aberrations in these optical components, such as diffraction, scattering, astigmatism, and coma, degrade the signal in both amplitude and across the field of view, resulting in greater noise contributions and cross talk among detected signals.

The analytical systems and devices in accordance with the present invention typically include a reaction region, vessel or zone that is either physically integrated with a detection component or sensor, or provided sufficiently proximal and in sensory communication with the detection component or sensor to improve performance.

Such devices have sought to take advantage of the proximity of the reaction region or vessel in which signal producing reactions are occurring, to the detector or detector element(s) that sense those signals, in order to take advantage of benefits presented by that proximity. As alluded to above, such benefits include the reduction of size, weight and complexity of the optical train, and as a result, increase the potential multiplex of a system, e.g., the number of different reaction regions that can be integrated and detected in a single device. Additionally, such proximity potentially provides benefits of reduced losses during signal transmission, reduced signal cross-talk from neighboring reaction regions, and reduced costs of overall systems that utilize such integrated devices, as compared to systems that utilize large free space optics and multiple cameras in signal collection and detection.

In the systems of the present invention, there are a number of design optimization criteria. For example, in the context of integrated detection systems, an over-arching goal is in the minimization of intervening optical elements that could interfere with the efficient conveyance of optical signals from the reaction region to the detector, as well as contribute to increased costs and space requirements for the system, by increasing the complexity of the optical elements between the reaction regions and the sensors.

Additionally, and with added importance for single molecule detection systems, it is also important to maximize the amount of optical signal that is detected for any given reaction event. In particular, in optical detection of individual molecular events, one is relying on a relatively small number of photons that correspond to the event of interest. While high quantum yield labeling groups, such as fluorescent dyes, can improve detectability, such systems still operate at the lower end of detectability of optical systems. Fluorescent dyes for analytical reactions are well known. Any suitable fluorescent dye can be used, for example, as described in 61/649,058 filed May 18, 2012—Heteroarylcyanine Dyes, US 20120058473—Molecular Adaptors for Dye Conjugates, US 20120077189—Scaffold-Based Polymerase Enzyme Substrates, US 20120052506—Cyanine Dyes, US 20120058469—Functionalized Cyanine Dyes (PEG), US 20120058482—Functionalized Cyanine Dyes ((Central Carbon), US 20100255488—Fret-Labeled Compounds and Uses Therefor, US 20090208957—Alternate Labelling Strategies for Single Molecule Sequencing In the context of the integrated devices and systems of the present invention, the size and complexity of the optical pathways poses a greater difficulty, as there is less available space in which to accomplish the goals of separation of excitation and signal, or separation of one signal from the next. Accordingly, the systems, devices and methods of the invention take advantage of simplified optical paths associated with the analyses being carried out, in order to optimize those analyses for the integrated nature of those devices and systems.

Figure 4:
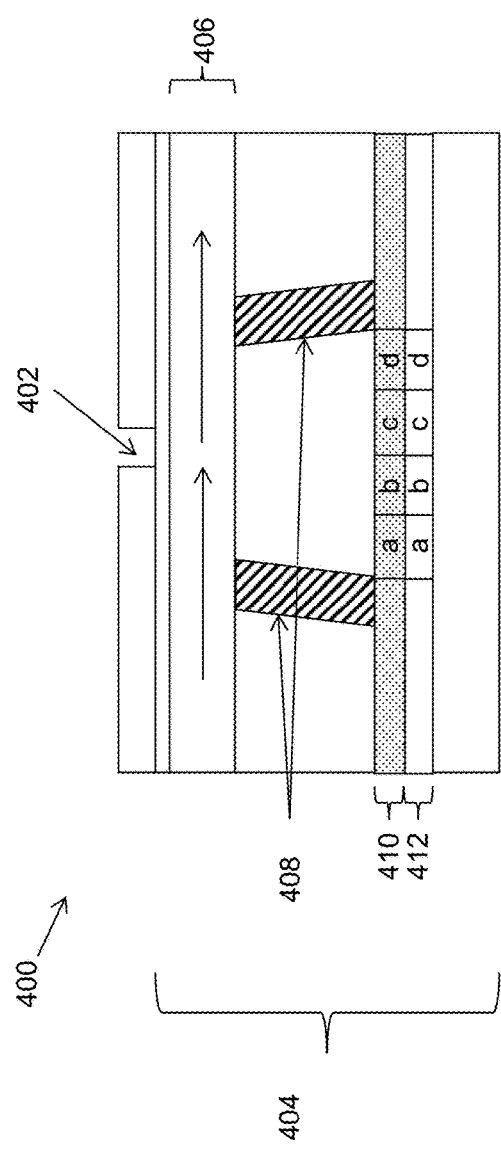
FIG. 4 shows an example of a device architecture for performing optical analyses.

FIG. 4 illustrates an example of a device architecture for performing optical analyses, e.g., nucleic acid sequencing processes or single molecule binding assay, that uses the filters of the present invention. As shown, an integrated device 400 includes a reaction region 402 that is defined upon a first substrate layer 404. As shown, the reaction region comprises a well 402 disposed in the substrate surface. Such wells may constitute depressions in a substrate surface or apertures disposed through additional substrate layers to an underlying transparent substrate, e.g., as used in zero mode waveguide arrays (See, e.g., U.S. Pat. Nos. 7,181,122 and 7,907,800). FIG. 4 illustrates a portion of a device having one reaction cell 402. Typically a device will have multiple reaction cells, for example thousands to millions or more reaction cells.

Excitation illumination is delivered to the reaction region from an excitation light source (not shown) that may be separate from or also integrated into the substrate. As shown, an optical waveguide (or waveguide layer) 406 is used to convey excitation light (shown by arrows) to the reaction region/well 402, where the evanescent field emanating from the waveguide 406 illuminates reactants within the reaction region 402. Use of optical waveguides to illuminate reaction regions is described in e.g., U.S. Pat. Nos. 7,820,983, 8,207,509, and 8,274,040, which is incorporated herein by reference for all purposes.

The integrated device 400 optionally includes light channeling components 408 to efficiently direct emitted light from the reaction regions to a detector layer 412 disposed beneath the reaction region. The detector layer will typically comprise multiple detector elements, for example the four detector elements 412a-d that are optically coupled to a given reaction region 402. For sequencing applications, often it is desirable to monitor four different signals in real time, each signal corresponding to one of the nucleobases. Although illustrated as a linear arrangement of pixels 412a-d, it will be appreciated that the detector elements may be arranged in a grid, n×n square, annular array, or any other convenient orientation. In some cases, each of the detector elements or channels will have a single pixel. In some cases, the detector elements will each comprise multiple pixels. The detector elements are connected electrically to conductors that extend out of the chip for providing electrical signals to the detector elements and for sending out signals from the detector elements.

Emitted signals from the reaction region 402 that impinge on these detector elements are then detected and recorded. As noted above, above each of the detector elements, each corresponding to a channel is disposed a color filter in filter layer 410. Here filter a corresponds to channel a, filter b corresponds to channel b, etc. As described in detail above, the set of filters is designed to allow for a high yield of captured photons, for example with each color filter having one or more blocking bands that block the signal from a portion of one or more of the spectrally distinct signals emitted from the reaction occurring in reaction region 402. As described herein, the filters are designed to allow a large percentage of the emitted photons while still discriminating between the four bases.

In some cases, optical elements are provided to selectively direct light from given sets of wavelengths to given detector elements. Typically, no specific light re-direction is used, such that the light reaching each of the filter layers the detector element is substantially the same.

The detector layer is then operably coupled to an appropriate circuitry, typically integrated into the substrate, for providing a signal response to a processor that is optionally included integrated within the same device structure or is separate from but electronically coupled to the detector layer and associated circuitry. Examples of types of circuitry are described in U.S. Published Patent Application No. 2012/0019828, previously incorporated herein.

Figure 5:
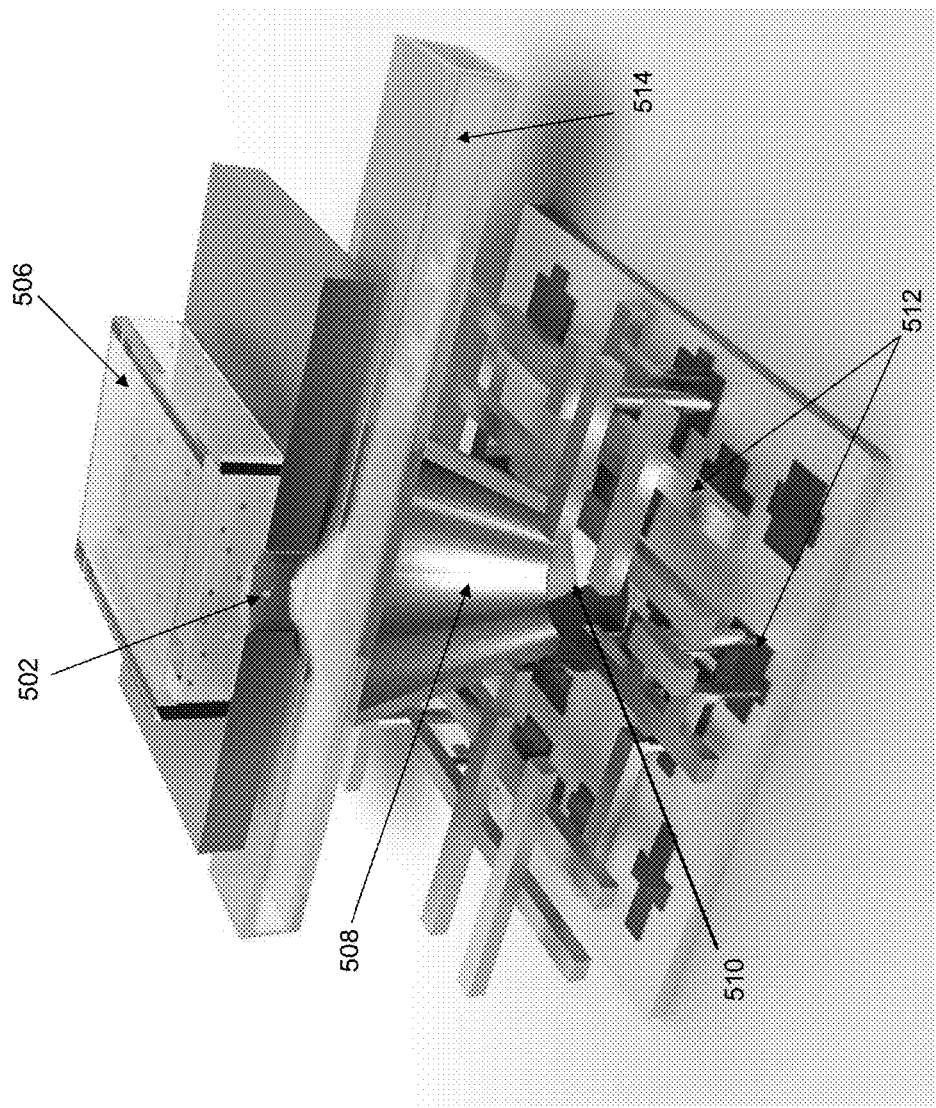
FIG. 5 shows an example of an integrated device used for four color analysis.

With reference to an integrated device used for four color analyses, as alluded to above, an exemplary structure is shown in FIG. 5. As shown, the analytical device includes a reaction cell 502 that is coupled with a reagent reservoir or fluid conduit 506 which delivers reactants to the reaction cell 502. The reaction cell can be a nanoscale well or zero mode waveguide. In some cases, the reaction cell will have a biomolecule such as a polymerase enzyme immobilized within it. The fluidic conduit can provide reagents across a number of reaction cells. Below the reaction cell is a waveguide for providing excitation illumination to the reagents within the reaction cell. While a waveguide is shown here, other optical elements such as those provided elsewhere herein can be used to provide light from under the reaction cell. The illumination light can be used to excite fluorescent emission from reagents with the reactor cell. The light emitted from the reaction cell is directed downward through a transmission layer, which acts to transmit the light from the reaction cell to the detector. In some cases, the transmission layer will have optical components to enhance the efficiency of the light transfer or modulate the light. In the analytical device of FIG. 5, an optical tunnel or conduit 508 is disposed in optical communication with the reaction cell 502, which is in turn in optical communication with sensing elements 510 in the detector, where the light reaching each of the 4 sensing elements on the detector passes through a different filter. As shown, each reaction cell is optically coupled to a detector or detector element that includes 4 regions or pixel subsets, each region or pixel subset including a filter layer, and each filter layer including at least one blocking band as described herein. Each filter sends the appropriate set of wavelengths of light to the appropriate pixel subset shown as a discriminating region in FIG. 5. The pixel subsets or sensor elements are coupled to appropriate electronic components 512, such as busses and interconnects, that make up the overall sensor or camera. The electronic components can also include processing elements for processing the signal from the detectors.

Accordingly, in certain aspects, the present invention provides optical detection systems that reduce the attenuation of optical signals emanating from the reaction region and ultimately, that reach the detector. This permits detection and signal discrimination that is based upon a greater amount of emitted and detected signal.

Analytical Instruments and systems

Some aspects of the invention are analytical instruments for carrying out the methods and for use with the analytical devices described herein. For example, in some cases, the analytical devices of the invention are part of an analytical instrument or analytical system. The analytical device can be removably coupled into an instrument. Reagents are brought into contact with the analytical device before and/or after the analytical device is coupled with the instrument. The system or instrument can provide electrical signals and/or illumination light to the analytical device, and can receive electrical signals from the detectors in the analytical device. The instrument or system typically has computers to manipulate, store, and analyze the data from the device. For example, the instrument can have the capability of identifying and sequences of added nucleotide analogs for performing nucleic acid sequencing. The identification can be carried out, for example, as described in U.S. Pat. No. 8,182,993, and U.S. Published Patent Application Nos. 2010/0169026, and 2011/0183320 which are incorporated herein by references for all purposes.

For example, the invention includes analytical instruments comprising any suitable analytical device describe herein, an illumination source for providing illumination light to the one or more waveguides, an electronic system for providing voltage and current to the detector, and for receiving signals from the detector; and a computer system for analyzing the signals from the detector to monitor the analytical reaction, for example to obtain sequence information about a template nucleic acid.

Planar Lightwave Circuits (PLCs)

In some aspects, the instant invention is used with optical delivery devices which are constructed with a plurality of integrated transmission waveguides to deliver optical energy from the optical input to the optical outputs. Such integrated devices are sometimes referred to as planar lightwave circuits (PLCs). PLCs are most typically found in telecommunications equipment, where they serve to couple and/or split optical signals from fiber optic cores, for the purpose of, for example, multiplexing/demultiplexing, optical branching, and/or optical switching. These more specific PLCs are also sometimes referred to as fiber spacing concentrators (FSCs). PLCs typically comprise multiple components that are directly fabricated into the integrated device, where the different components provide the desired functionality. For example, a PLC may comprise one or more waveguides, one or more splitters, one or more taps, one or more photodetectors, and one or more fibers, ideally polarization-maintaining fibers. The fibers and PLCs used in telecommunications applications typically transmit light in the infrared range, most commonly at wavelengths of about 1310 nm or about 1550 nm. In some cases, lower cost electronics such as light-emitting diodes (LEDs) and vertical-cavity surface-emitting lasers (VCSELs) may be used in devices comprising PLCs, such as FSCs.

In contrast to the PLCs used to transmit optical telecommunication signals, however, the instant optical delivery devices are designed for the efficient transmission of shorter wavelengths of light. In particular, the optical illumination for fluorescent analysis, for example in DNA sequencing reactions with fluorescently-labeled DNA reagents, is typically in the visible range, most commonly in the range from about 450 nm to about 650 nm. The waveguides and other components of the optical delivery devices disclosed herein, and incorporated into the instant systems for DNA sequencing, are therefore preferably designed and scaled to transmit optical energy efficiently in the visible range. In some embodiments, the wavelengths range from about 450 nm to about 700 nm. In more specific embodiments, the wavelengths range from about 500 nm to 650 nm or even from about 500 nm to about 600 nm. In some specific embodiments, the wavelengths are from about 520 nm to about 540 nm, for example, approximately 532 nm. In other specific embodiments, the wavelengths are from about 620 nm to about 660 nm, for example, approximately 635 nm or 650 nm. In some embodiments, a combination of visible wavelengths may be transmitted within the devices.

Figure 6:
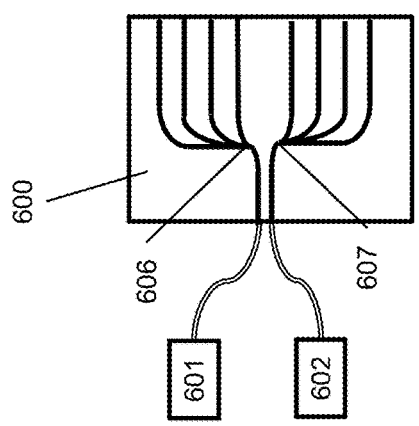
FIG. 6 shows a representative planar lightwave circuit.

FIG. 6 illustrates a representative PLC for use in conjunction with the invention. FIG. 6 shows an representative embodiment having a device 600. Visible light from two lasers (601 and 602) is delivered to a PLC coupler chip by two optical fibers, where each fiber is directed into a 1×4 splitter (606 and 607) built into the device to provide 8 optical outputs. Input lasers are typically interfaced to the PLC using fiber pigtails or the like, and the optional inclusion of splitters within the PLC may simplify assembly of the systems and decrease their cost by limiting the number of fiber interconnections required.

EXAMPLES

Illumination and Measurement from Waveguides

Figure 7:
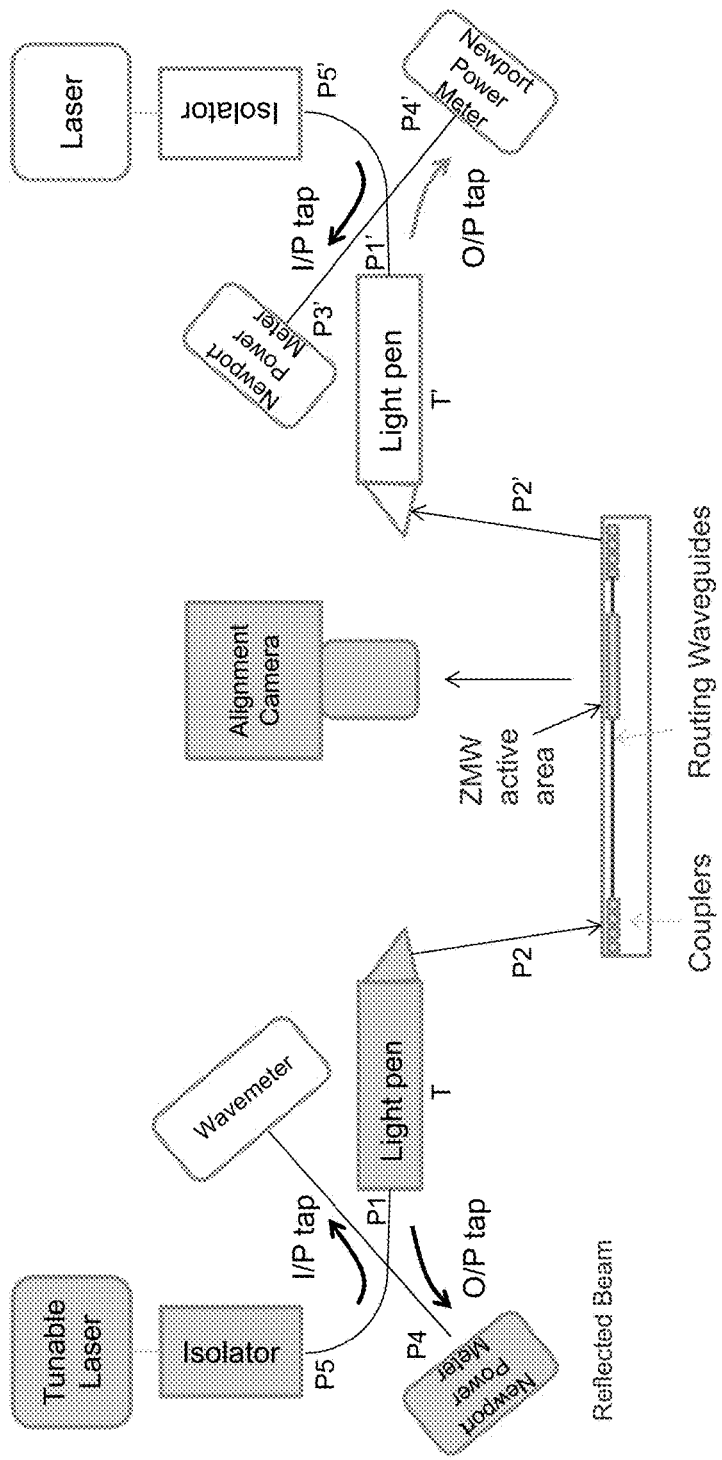
FIG. 7 shows a setup used for sending light into a waveguide and measuring the amount of light transmitted as well as the amount of reflected over time.

FIG. 7 shows a setup used for sending light into a waveguide and measuring the amount of light transmitted as well as the amount of reflected over time. The light can either be delivered from one side using one of the lasers or from both sides using both lasers. The alignment camera measures light sent through the waveguides and then coupled out of the chip. The chip has a zero mode waveguide (ZMW) region for carrying out fluorescent analyses such as single molecule real time sequencing as described herein.

Time Dependent Back Reflection

Figure 8:
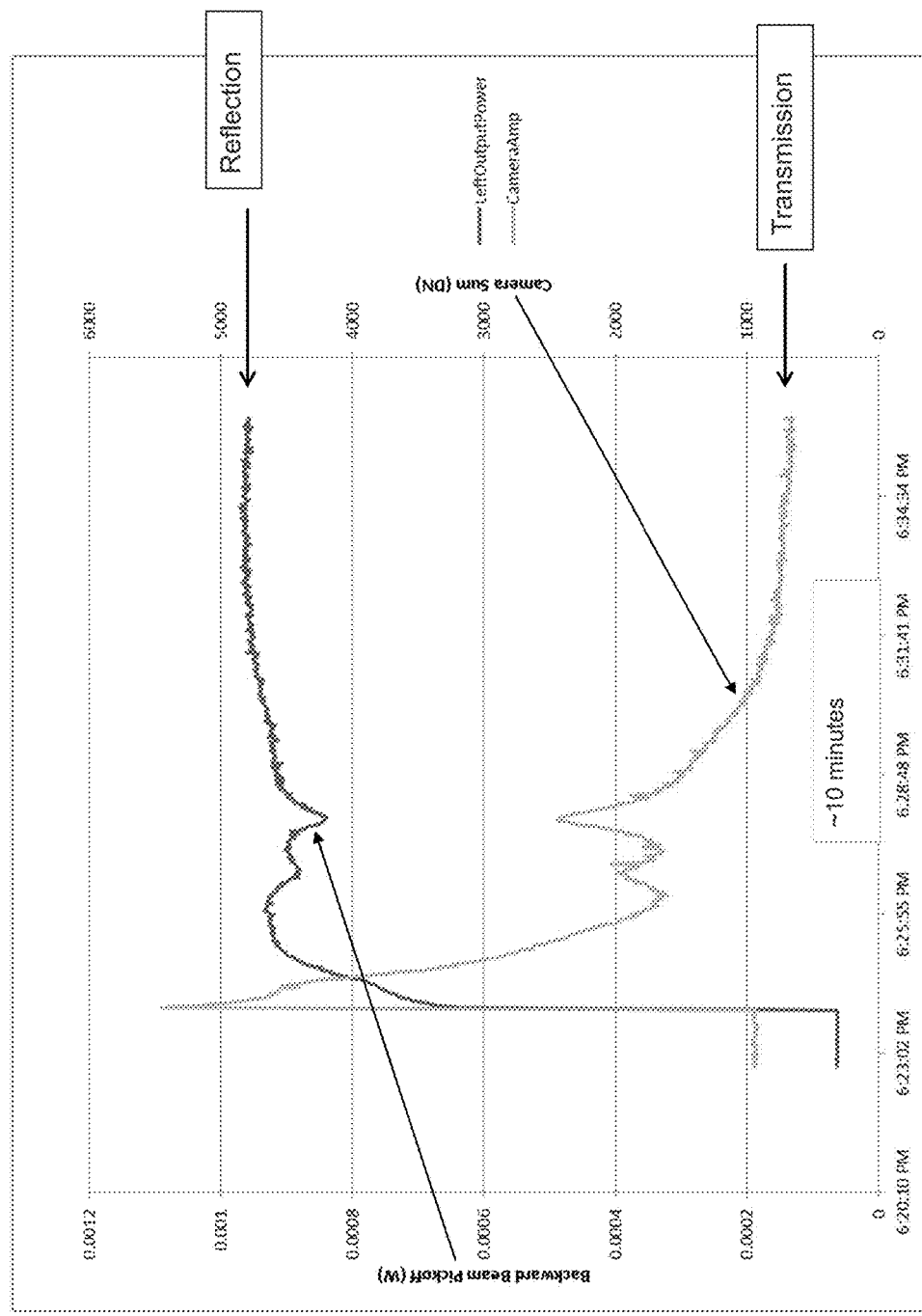
FIG. 8 shows a set of measurements that illustrate the time dependent back reflection.

FIG. 8 shows a set of measurements that illustrate the time dependent back reflection. Light is sent into the waveguide at about 532 nm. The top curve, axis to the left shows reflected light over time. The lower curve, axis to the left shows transmitted light. It can be seen that over time there is a build up in back reflection that occurs at the expense of transmitted light.

Use of Temperature to Reduce Back Reflection and Improve Transmission

Figure 9:
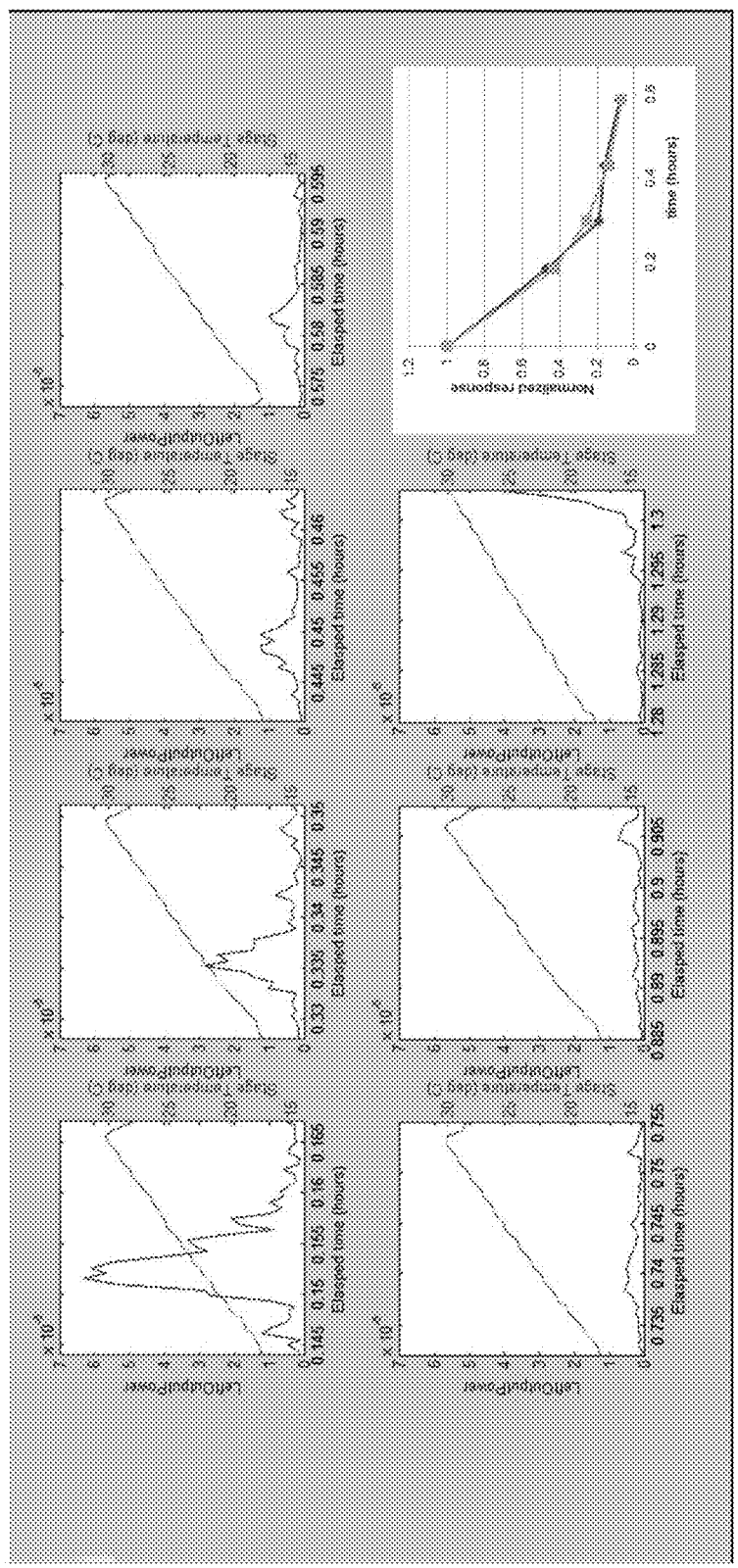
FIG. 9 shows how a change in temperature resulted in the reduction of back reflection over time.

FIG. 9 shows how a change in temperature from 22 degree to 30 degrees resulted in the reduction of back reflection over time. This demonstrates erasure of the grating with a temperature change. The peak at 22° C. diminished in height. It did not move spectrally. A new peak was forming at 30° C. As seen in the bottom right, the decay is approximately exponential.

Use of Wavelength Modulation to Reduce or Remove Backscatter

Figure 10:
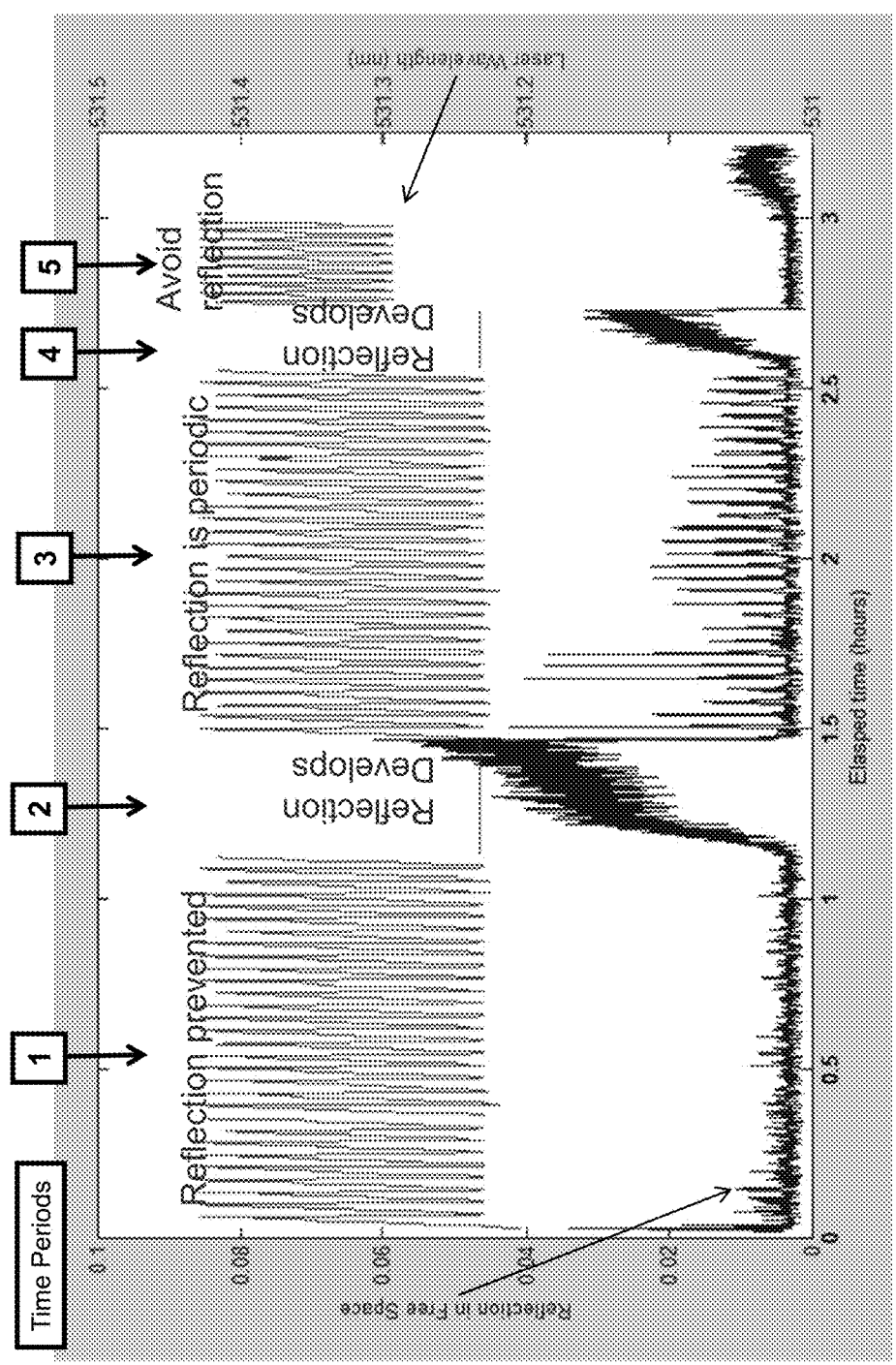
FIG. 10 shows how a modulation in wavelength prevents the buildup of back reflection and can be used to avoid it.
Figure 11:
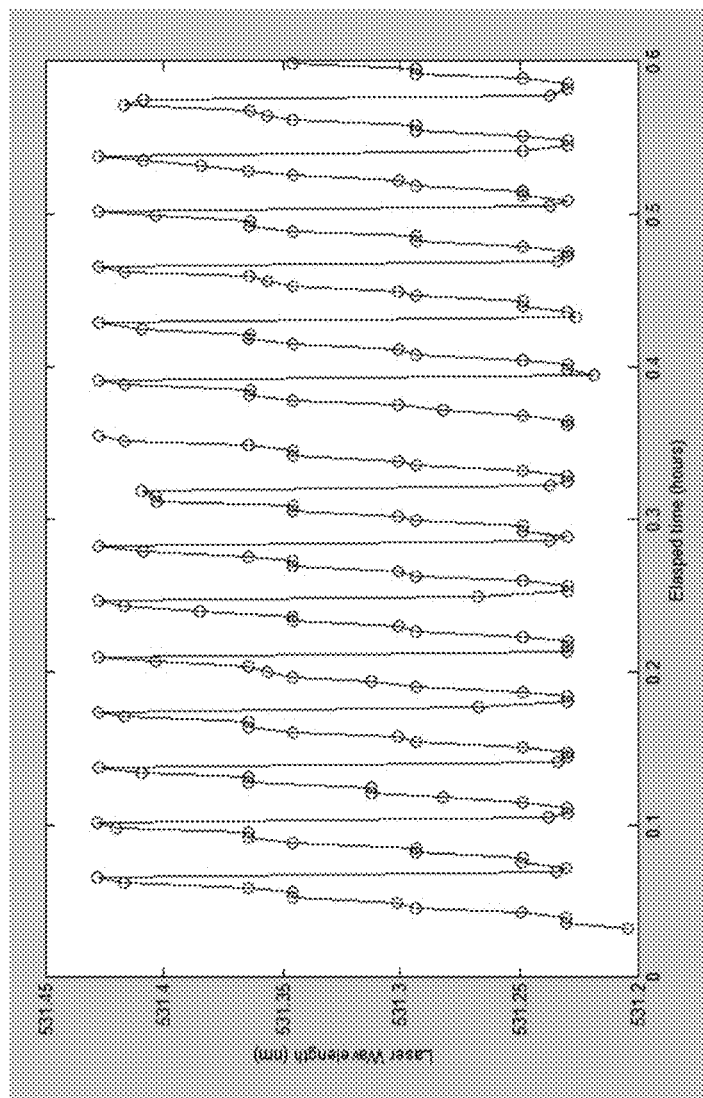
FIG. 11 shows a wavelength modulation scheme with approximately 6 different wavelengths periodically addressed.
Figure 12:
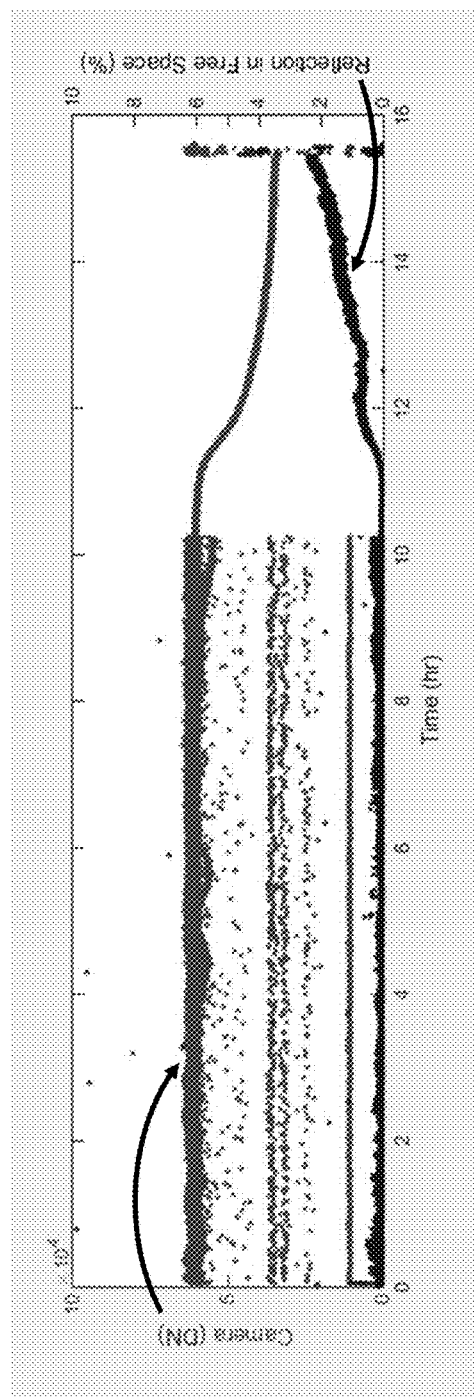
FIG. 12 shows how wavelength variation can hold down back reflection, thereby improving transmission over longer time periods.

FIG. 10 shows how a modulation in wavelength prevents the buildup of back reflection and can be used to avoid it. The upper curve (left axis) is the laser wavelength, adjusted over about 200 picometers. The lower curve (right axis) is the measurement of back reflection. In time period 1, the buildup of a back reflection is prevented over a time period of about 1 hour. In time period 2, the wavelength is held constant, at which time the characteristic back reflection over time develops. In time period 3, the modulation is re-instated, lowering the back reflection. The back reflection is now periodic. We see reflection where the wavelength of the laser is brought back into the range of the wavelength at which the back reflection built up. This provides strong evidence that it is a Bragg grating that is being formed over time. In time period 4, again the modulation is turned off, and the back reflection begins to rise again. In period 5, the range of wavelength modulation is changed such that the rang no longer includes wavelengths near where the back reflection build up occurred. This is even stronger evidence of the formation of a Bragg grating within the waveguide. FIG. 11 shows a close up of the wavelength modulation used with approximately 6 different wavelengths periodically addressed. FIG. 12 shows how the wavelength variation can hold down back reflection, thereby improving transmission over longer time periods. Here, there was 20 mW beam power, 300 WL cycles overnight and another 3 cycles in the morning. The variation/excursion of camera signals during laser toggling may due to the variation of input power. The bottom curve (axis on the right) is the measurement of back reflection. The top curve (right axis) shows the measurement of transmission using a camera above the chip. It can be seen that wavelength modulation for 10 hours prevented the rise of the backscatter. After 10 hours the wavelength modulation was removed resulting in the rise in the level of backscatter, and concomitant drop in transmission. Near the end of the run (between 15 and 16 hours) the wavelength modulation was re-introduced, resulting in a drop in reflection and rise in transmission.

The invention claimed is:

1. A method for improving light transmission through a chip comprising at least one waveguide comprising:
providing a chip comprising at least one waveguide; and
providing to the waveguide on the chip illumination light from a laser, wherein the wavelength of the illumination provided by the laser is modulated over time within a range of wavelengths, wherein the range of wavelength modulation is less than 1 nm, whereby the waveguide exhibits less back reflection than when the laser wavelength is not modulated.

2. The method of claim 1 wherein the laser wavelength is between about 500 nm and about 650 nm.

3. The method of claim 1 wherein the range of wavelength modulation is less than 500 picometers.

4. The method of claim 1 wherein the range of wavelength modulation is less than 250 picometers.

5. The method of claim 1 wherein the frequency of wavelength modulation is less than about 1 Hz.

6. The method of claim 1 wherein the frequency of wavelength modulation is less than about 0.1 Hz.

7. The method of claim 1 wherein the wavelength modulation is carried out by cycling the laser through more than two different wavelengths.

8. The method of claim 1 wherein the wavelength modulation is carried out by cycling the laser through 3 to 30 different wavelengths.

9. The method of claim 1 wherein the wavelength modulation is carried out by randomly addressing wavelengths within the range of wavelength modulation.

10. The method of claim 1 wherein the wavelength modulation is carried out by monitoring a back reflection level and changing the laser wavelength if the back reflection level exceeds a threshold level.

11. The method of claim 10 wherein the threshold level is between 0.1% and 2% of the intensity of complete back reflection.

12. The method of claim 10 wherein the back reflection level is determined by measuring a drop in forward transmission.

13. The method of claim 1 wherein the waveguide comprises a SiON core.

14. The method of claim 1 wherein the waveguide comprises a core that is surrounded by silicon dioxide.

15. The method of claim 1 wherein the chip comprises a detector.

16. The method of claim 15 wherein the detector comprises a CMOS detector.

17. The method of claim 1 wherein the waveguides provide illumination to nanoscale wells on the chip comprising fluorescent species.

18. The method of claim 1 wherein the chip comprises a semiconductor chip.

* * * * *